US012642812B2

(12) United States Patent
Bermond et al.

(10) Patent No.: US 12,642,812 B2
(45) Date of Patent: Jun. 2, 2026

(54) NICOTINAMIDE MONONUCLEOTIDE DERIVATIVES AND USE THEREOF IN THE TREATMENT AND PREVENTION OF AN ANTINEOPLASTIC-INDUCED TOXICITY

(71) Applicant: NUVAMID SA, Epalinges (CH)

(72) Inventors: Guillaume Bermond, Epalinges (CH); Laurent Garçon, Epalinges (CH)

(73) Assignee: NUVAMID SA, Epalinges (CH)

( * ) Notice: Subject to any disclaimer, the term of this patent is extended or adjusted under 35 U.S.C. 154(b) by 620 days.

(21) Appl. No.: 18/040,182

(22) PCT Filed: Aug. 6, 2021

(86) PCT No.: PCT/EP2021/071998
§ 371 (c)(1),
(2) Date: Feb. 1, 2023

(87) PCT Pub. No.: WO2022/029287
PCT Pub. Date: Feb. 10, 2022

(65) Prior Publication Data

US 2023/0321131 A1 Oct. 12, 2023

(30) Foreign Application Priority Data

Aug. 7, 2020 (EP) .................................... 20190010
Dec. 18, 2020 (EP) .................................... 20215832

(51) Int. Cl.

*A61K 31/7084* (2006.01)
*A61K 31/706* (2006.01)
*A61K 45/06* (2006.01)
*A61P 9/00* (2006.01)
*A61P 39/00* (2006.01)

(52) U.S. Cl.
CPC ........ *A61K 31/7084* (2013.01); *A61K 31/706* (2013.01); *A61K 45/06* (2013.01); *A61P 9/00* (2018.01); *A61P 39/00* (2018.01)

(58) Field of Classification Search
None
See application file for complete search history.

(56) References Cited

FOREIGN PATENT DOCUMENTS

WO 2006105440 A2 10/2006
WO 2007008548 A2 1/2007
WO 2015186114 A1 12/2015
WO 2017096246 A1 6/2017
WO 2018002215 A1 1/2018
WO 2021123388 A1 6/2021
WO 2021176093 A1 9/2021

OTHER PUBLICATIONS

Zheng, Dong, et al. "Nicotinamide riboside promotes autolysosome clearance in preventing doxorubicin-induced cardiotoxicity." Clinical Science 133.13 (2019): 1505-1521.*
Octavia, Yanti, et al. "Doxorubicin-induced cardiomyopathy: from molecular mechanisms to therapeutic strategies." Journal of molecular and cellular cardiology 52.6 (2012): 1213-1225.*
Zheng et al., "Nicotinamide Riboside Promotes Autolysosome Clearance in Preventing Doxorubicin-Induced Cardiotoxicity", Clinical Science, The Author(s), Portland Press Limited, Jul. 15, 2019, vol. 133, pp. 1505-1521.
Dang, "Boosting Cellular NAD+ Concentration with Nicotinamide Mononucleotide Prevents Doxorubicin-Induced Cardiotoxicity", Electronic Thesis and Dissertation Repository, Western Graduate & Postdoctoral Studies, Western University, Abstract published on Aug. 27, 2020, Master Thesis published on Sep. 30, 2022, 82 pages.
International Search Report issued on Nov. 5, 2021, in corresponding International Application No. PCT/EP2021/071998, 5 pages.
International Written Opinion issued on Nov. 5, 2021, in corresponding International Application No. PCT/EP2021/071998, 8 pages.
Prasad et al., "Increased oxidative stress, inflammation, and glutamate: potential preventive and therapeutic targets for hearing disorders", Mechanisms of Ageing and Development, Nov. 29, 2019, vol. 185 No. 111191, 14 pages.
Lee et al., "Cardiotoxicity of contemporary breast cancer treatments", Curr. Treat. Options in Oncol., May 9, 2019, vol. 20 No. 51, 16 pages.
Mehmel et al., "Nicotinamide riboside—The current state of research and therapeutic uses", Nutrients, May 31, 2020, vol. 12 No. 1616, 22 pages.
Oppenheimer et al., "Proton Magnetic Resonance Study of the Intramolecular Association and Conformation of the Alpha and Beta Pyridine Mononucleotides and Nucleosides", Biochemistry, 1976, vol. 15, No. 18, pp. 3981-3989.

(Continued)

*Primary Examiner* — Patrick T Lewis
(74) *Attorney, Agent, or Firm* — Maier & Maier, PLLC

(57) ABSTRACT

Nicotinamide mononucleotide derivatives of Formula (I)

(I)

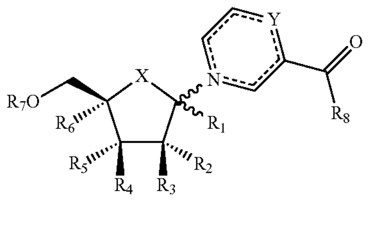

for use in the treatment and/or prevention of an antineoplastic-induced toxicity. Also, pharmaceutical compositions that include compounds of Formula (I) for use in the treatment and/or prevention of an antineoplastic-induced toxicity selected from cardiotoxicity, nephrotoxicity, haematotoxicity, hepatotoxicity, lymphoid toxicity, gastrointestinal toxicity, dermal toxicity, reproductive toxicity, bone toxicity, genetic toxicity and bladder toxicity.

9 Claims, 3 Drawing Sheet

(56) References Cited

OTHER PUBLICATIONS

Nalin, "Nicotinamide Mononucleotide Imparts Protection Against Doxorubicin-Induced Cardiotoxicity by Maintaining Lysosomal Acidification", Electronic Thesis and Dissertation Repository 7195, Western University, Master Thesis, Aug. 26, 2020, 105 pages.

* cited by examiner

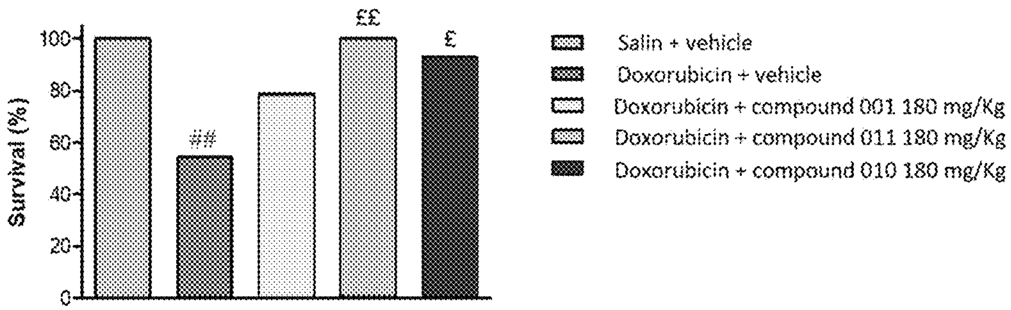
FIG. 1
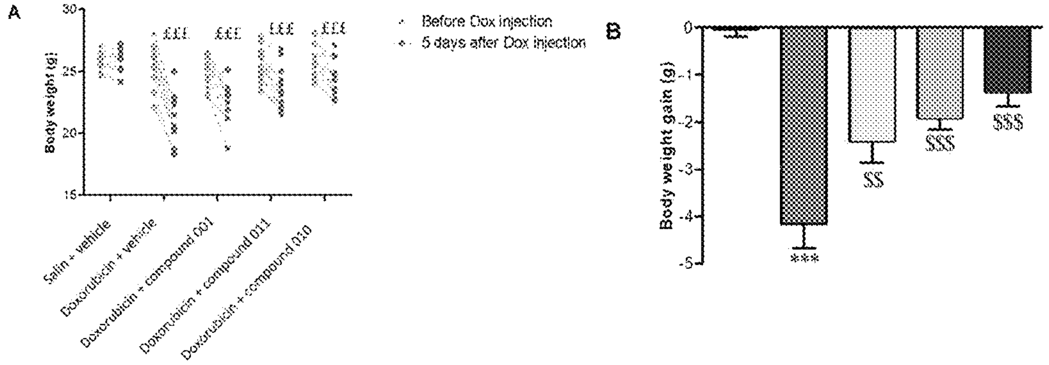
FIG. 2 (A and B)
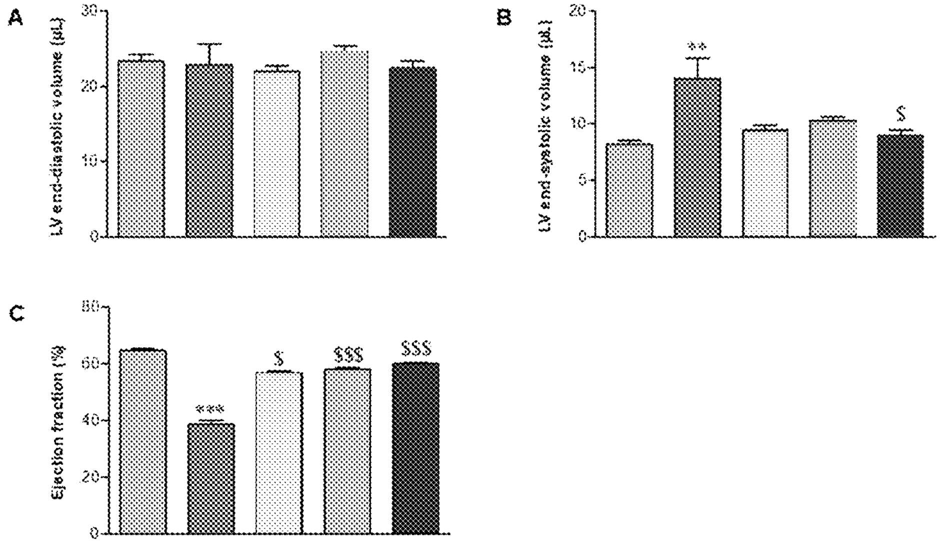
FIG. 3 (A, B and C)

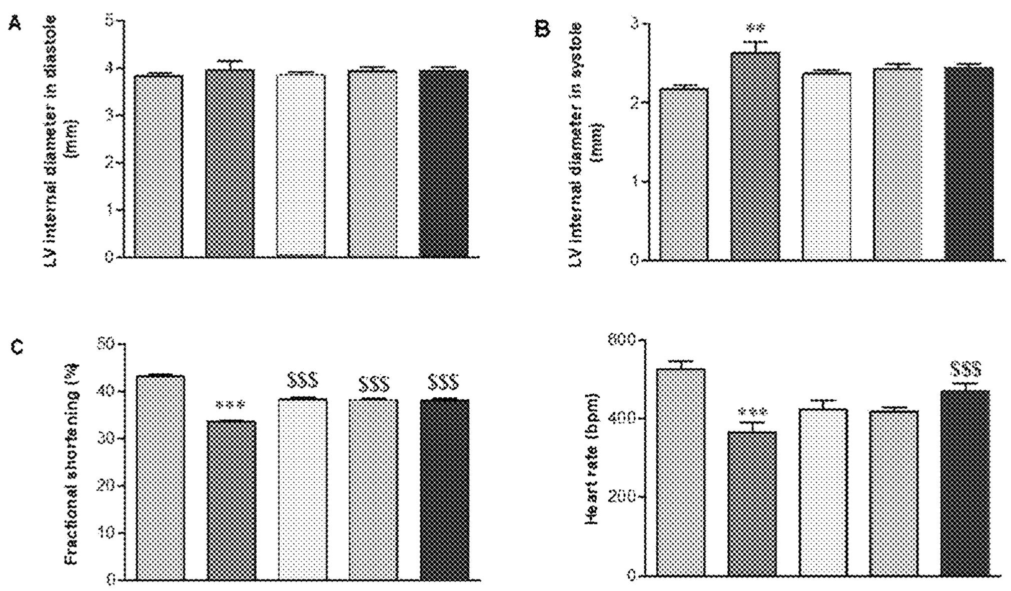
FIG. 4 (A, B, C and D)
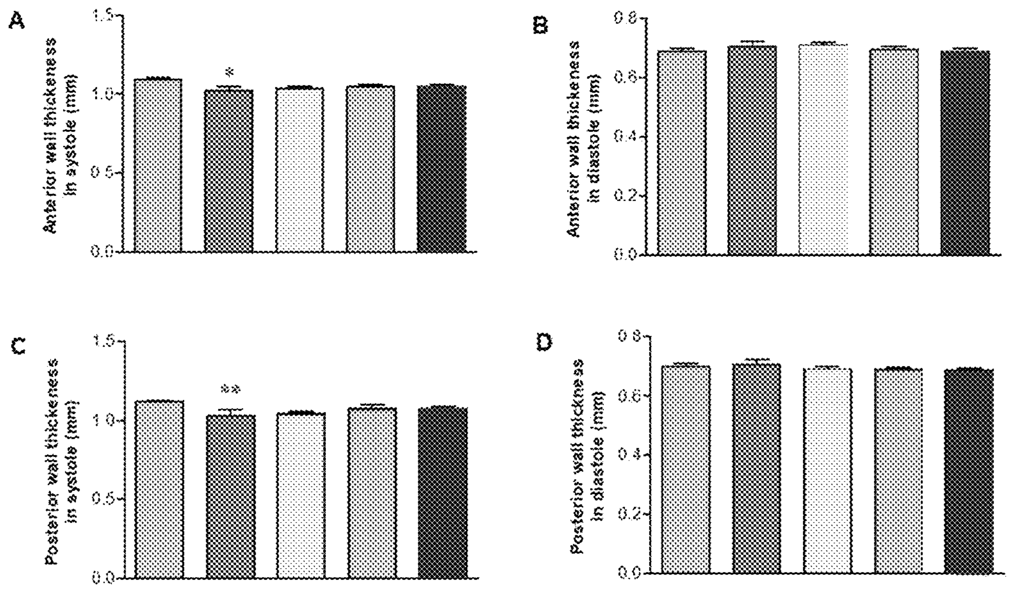
FIG. 5 (A, B, C and D)

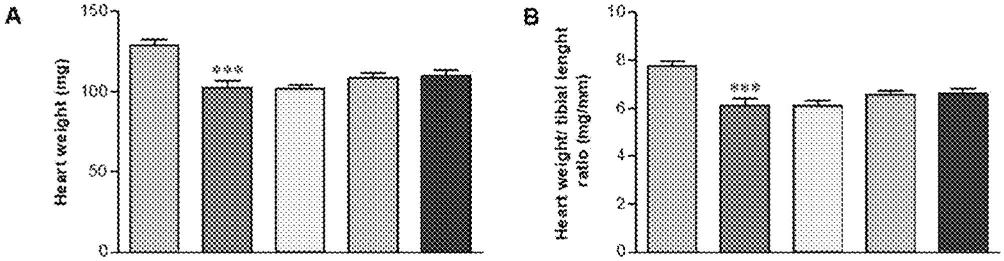
FIG. 6 (A and B)
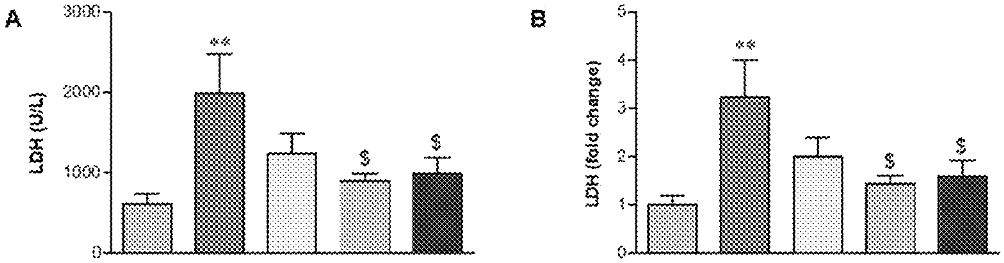
FIG. 7 (A and B)

NICOTINAMIDE MONONUCLEOTIDE DERIVATIVES AND USE THEREOF IN THE TREATMENT AND PREVENTION OF AN ANTINEOPLASTIC-INDUCED TOXICITY

FIELD

The present invention relates to nicotinamide mononucleotide derivatives compounds for use in the treatment and/or prevention of an antineoplastic-induced toxicity.

BACKGROUND

Drug-induced toxicities, such as cardiotoxicity, nephrotoxicity, neurotoxicity, haematotoxicity or hepatotoxicity, are an important cause of recall of compounds in preclinical and clinical development.

Remarkably, almost 10% of drugs in the last four decades have been recalled from the clinical market worldwide due to cardiovascular safety concerns, e.g., rofecoxib, tegaserod, and sibutramine, and despite the great efforts to reveal cardiotoxicity in the preclinical phase of development of medicinal products, cardiotoxicity continues to lead safety concerns mainly because of lack of sufficient knowledge of the mechanisms of cardiotoxicity.

While all therapeutic drug classes have unanticipated toxicities, toxicity induced by chronically administered drugs, such as neurologic/psychiatric agents and anticancer chemotherapeutic agents, represents a major problem because toxicity may become evident only after long-term accumulation of the drug or its metabolites.

Especially, drug-induced cardiotoxicity, commonly in the form of cardiac muscle dysfunction that may progress to heart failure, represents a major adverse effect of some common traditional antineoplastic agents, e.g., anthracyclines, cyclophosphamide, fluorouracil (5-FU) and taxanes, as well as newer agents such as biological monoclonal antibodies, e.g., trastuzumab, bevacizumab and nivolumab; tyrosine kinase inhibitors, e.g., sunitinib and nilotinib; antiretroviral drugs, e.g., zidovudine; antidiabetics, e.g., rosiglitazone; as well as some recreative drugs such as alcohol, cocaine, methamphetamine, ecstasy and synthetic cannabinoids.

Currently, cancer is shown to affect more than one in three people in their lifetime, and along with cardiovascular diseases, they are the two leading causes of death in developed nations. Thanks to improvement in cancer pharmacotherapy, a current overall 10-year cancer survival stands at 50% across the 20 most common malignancies and it is estimated that 33% of long cancer survivors die of heart disease.

Anthracyclines-induced cardiotoxicity and especially cardiomyopathy induced by doxorubicin (DOX) is considered an extremely serious adverse effect of oncologic treatment.

Doxorubicin is among the most widely used drugs for the treatment of both adult and child cancers. DOX-induced cardiotoxicity manifests in several forms, ranging from asymptomatic electrocardiography (ECG)-changes to decompensated cardiomyopathy characterized by decreased left ventricular ejection fraction. According to their clinical manifestation, these cardiotoxic events can be classified into three types: (1) acute, occurring during or immediately after treatment; (2) early-onset chronic progressive cardiotoxicity, occurring within 1 year after exposure to chemotherapeutic treatment; and (3) late-onset chronic progressive cardiotoxicity, occurring 1 or more years after the end of treatment.

Many studies have explored pathophysiology and mechanisms of doxorubicin-induced cardiotoxicity, however, the exact mechanism remains unclear, though it is likely to be multifactorial.

Mitochondrial damage and overt ROS production have been considered as the primary causes of cardiotoxicity. However, the use of ROS inhibitors for treating DOX cardiomyopathy has not been successful, and at present no effective therapy is available to treat an established DOX-cardiomyopathy.

To date, standard management during anthracycline-based chemotherapy involves cardiac function assessment prior to treatment, monitoring potential cardiotoxicity during the therapy, as well as a long-term follow-up after the chemotherapy is completed.

Some protocols have been proposed to ameliorate or treat doxorubicin-/drug-induced cardiotoxicity including the use of epirubicin instead of doxorubicin; the concomitant use of the antioxidant and iron chelator dexrazoxane, angiotensin-converting enzyme inhibitors, angiotensin receptor blockers, beta blockers, ranolazine, metformin and hydroxymethylglutaryl-coenzyme A reductase inhibitors; the use of antioxidants such as self-nanoemulsifying formulation of quercetin, Q10 coenzyme, pyrroloquinoline quinone, vitamin E, and carnitine.

However, the effectiveness of these drugs varies depending on the patient and the clinical manifestation observed and further studies need to be done to assess whether the beneficial effect observed on cardiac function is preserved over the years.

Therefore, there is an urgent need for effective and safe prophylactic and/or therapeutic treatments of drug-induced toxicity, in particular antineoplastic-induced toxicity.

The purpose of the present invention is thus to provide a safe prophylactic and/or therapeutic treatment of an antineoplastic-induced toxicity by providing nicotinamide mononucleotide of formula 001 and derivatives thereof for use in the treatment and/or prevention of an antineoplastic-induced toxicity, in particular an antineoplastic-induced cardiotoxicity.

The Applicant surprisingly found that the nicotinamide mononucleotide derivatives according to the invention are potent agents to treat and/or prevent an antineoplastic-induced cardiotoxicity, especially doxorubicin-induced cardiotoxicity, and are well tolerated.

SUMMARY

This invention thus relates to a compound of Formula (I), (I)

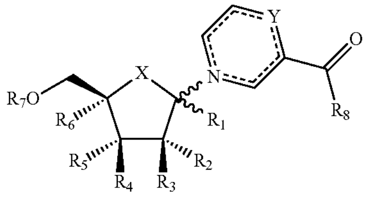

or a pharmaceutically acceptable salt or solvate thereof; wherein:

X is selected from O, $CH_2$, S, Se, CHF, $CF_2$ and $C{=}CH_2$;

$R_1$ is selected from H, azido, cyano, $(C_1\text{-}C_8)$alkyl, $(C_1\text{-}C_8)$thio-alkyl, $(C_1\text{-}C_8)$heteroalkyl and OR; wherein R is selected from H and $(C_1\text{-}C_8)$alkyl;

$R_2$, $R_3$, $R_4$ and $R_5$ are independently selected from H, halogen, azido, cyano, hydroxyl, $(C_1\text{-}C_{12})$alkyl, $(C_1\text{-}C_{12})$thio-alkyl, $(C_1\text{-}C_{12})$heteroalkyl, $(C_1\text{-}C_{12})$haloalkyl and OR; wherein R is selected from H, $(C_1\text{-}C_{12})$alkyl, —C(O)$(C_1\text{-}C_{12})$alkyl, —C(O)NH$(C_1\text{-}C_{12})$alkyl, —C(O)O$(C_1\text{-}C_{12})$alkyl, —C(O)aryl, —C(O)$(C_1\text{-}C_{12})$alkyl-$(C_5\text{-}C_{12})$aryl, —C(O)NH$(C_1\text{-}C_{12})$alkyl-$(C_5\text{-}C_{12})$aryl, —C(O)O$(C_1\text{-}C_{12})$alkyl-$(C_5\text{-}C_{12})$aryl and —C(O)CH$R_{AA}$$NH_2$; wherein $R_{AA}$ is a side chain selected from a proteinogenic amino acid;

$R_6$ is selected from H, azido, cyano, $(C_1\text{-}C_8)$alkyl, $(C_1\text{-}C_8)$thio-alkyl, $(C_1\text{-}C_8)$heteroalkyl and OR; wherein R is selected from H and $(C_1\text{-}C_8)$alkyl;

$R_7$ is selected from H, P(O)$R_9R_{10}$, P(S)$R_9R_{10}$ and

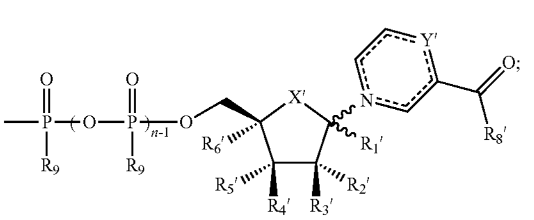

wherein:

$R_9$ and $R_{10}$ are independently selected from OH, $OR_{11}$, $NR_{13}R_{14}$, $(C_1\text{-}C_8)$alkyl, $(C_2\text{-}C_8)$alkenyl, $(C_2\text{-}C_8)$alkynyl, $(C_3\text{-}C_{10})$cycloalkyl, $(C_5\text{-}C_{12})$aryl, $(C_5\text{-}C_{12})$aryl-$(C_1\text{-}C_8)$alkyl, $(C_1\text{-}C_8)$alkyl-$(C_5\text{-}C_{12})$aryl, $(C_1\text{-}C_8)$heteroalkyl, $(C_3\text{. }C_8)$heterocycloalkyl, $(C_5\text{-}C_{12})$heteroaryl and NHC$R_\alpha R_{\alpha'}$—C(O)$OR_{12}$; wherein:

$R_{11}$ is selected from $(C_1\text{-}C_{10})$alkyl, $(C_3\text{-}C_{10})$cycloalkyl, $(C_5\text{-}C_{12})$aryl, $(C_1\text{-}C_{10})$alkyl-$(C_5\text{-}C_{12})$aryl, substituted $(C_5\text{-}C_{12})$aryl, $(C_1\text{-}C_{10})$heteroalkyl, $(C_1\text{-}C_{10})$haloalkyl, —$(CH_2)_m$C(O)$(C_1\text{-}C_{15})$alkyl, —$(CH_2)_m$OC(O)$(C_1\text{-}C_{15})$alkyl, —$(CH_2)_m$OC(O)O$(C_1\text{-}C_{15})$alkyl, —$(CH_2)_m$SC(O)$(C_1\text{-}C_{15})$alkyl, —$(CH_2)_m$C(O)O$(C_1\text{-}C_{15})$alkyl, —$(CH_2)_m$C(O)O$(C_1\text{-}C_{15})$alkyl-$(C_5\text{-}C_{12})$aryl; wherein m is an integer selected from 1 to 8; and —P(O)(OH)OP(O)$(OH)_2$; and an internal or external counterion;

$R_{12}$ is selected from hydrogen, $(C_1\text{-}C_{10})$alkyl, $(C_2\text{-}C_8)$alkenyl, $(C_2\text{-}C_8)$alkynyl, $(C_1\text{-}C_{10})$haloalkyl, $(C_3\text{-}C_{10})$cycloalkyl, $(C_3\text{-}C_{10})$heterocycloalkyl, $(C_5\text{-}C_{12})$aryl, $(C_1\text{-}C_4)$alkyl-$(C_5\text{-}C_{12})$aryl and $(C_5\text{-}C_{12})$heteroaryl; wherein said aryl or heteroaryl groups are optionally substituted by one or two groups selected from halogen, trifluoromethyl, $(C_1\text{-}C_6)$alkyl, $(C_1\text{-}C_6)$alkoxy and cyano;

$R_{13}$ and $R_{14}$ are independently selected from H, $(C_1\text{-}C_8)$alkyl and $(C_1\text{-}C_8)$alkyl-$(C_5\text{-}C_{12})$aryl; and $R_\alpha$ and $R_{\alpha'}$ are independently selected from an hydrogen, $(C_1\text{-}C_{10})$alkyl, $(C_2\text{-}C_{10})$alkenyl, $(C_2\text{-}C_{10})$alkynyl, $(C_3\text{-}C_{10})$cycloalkyl, $(C_1\text{-}C_{10})$thio-alkyl, $(C_1\text{-}C_{10})$hydroxyalkyl, $(C_1\text{-}C_{10})$alkyl-$(C_5\text{-}C_{12})$aryl, $(C_5\text{-}C_{12})$aryl, —$(CH_2)_3$NHC(═NH)$NH_2$, (1H-indol-3-yl)methyl, (1H-imidazol-4-yl)methyl and a side chain selected from a proteinogenic or non-proteinogenic amino acid; wherein said aryl groups are optionally substituted with a group selected from hydroxyl, $(C_1\text{-}C_{10})$alkyl, $(C_1\text{-}C_6)$alkoxy, halogen, nitro and cyano; or $R_9$ and $R_{10}$ together with the phosphorus atom to which they are attached form a 6-membered ring wherein —$R_9$-$R_{10}$— represents —O—$CH_2$—$CH_2$—CHR—O—; wherein R is selected from hydrogen, $(C_5\text{-}C_6)$aryl and $(C_5\text{-}C_6)$heteroaryl; wherein said aryl or heteroaryl groups are optionally substituted by one or two groups selected from halogen, trifluoromethyl, $(C_1\text{-}C_6)$alkyl, $(C_1\text{-}C_6)$alkoxy and cyano;

X' is selected from O, $CH_2$, S, Se, CHF, $CF_2$ and C═$CH_2$;

$R_{1'}$ is selected from H, azido, cyano, $(C_1\text{-}C_8)$alkyl, $(C_1\text{-}C_8)$thio-alkyl, $(C_1\text{-}C_8)$heteroalkyl and OR; wherein R is selected from H and $(C_1\text{-}C_8)$alkyl;

$R_{2'}$, $R_{3'}$, $R_{4'}$ and $R_{5'}$ are independently selected from H, halogen, azido, cyano, hydroxyl, $(C_1\text{-}C_{12})$alkyl, $(C_1\text{-}C_{12})$thio-alkyl, $(C_1\text{-}C_{12})$heteroalkyl, $(C_1\text{-}C_{12})$haloalkyl and OR; wherein R is selected from H, $(C_1\text{-}C_{12})$alkyl, —C(O)$(C_1\text{-}C_{12})$alkyl, —C(O)NH$(C_1\text{-}C_{12})$alkyl, —C(O)O$(C_1\text{-}C_{12})$alkyl, —C(O)aryl, —C(O)$(C_1\text{-}C_{12})$alkyl-$(C_5\text{-}C_{12})$aryl, —C(O)NH$(C_1\text{-}C_{12})$alkyl-$(C_5\text{-}C_{12})$aryl, —C(O)O$(C_1\text{-}C_{12})$alkyl-$(C_5\text{-}C_{12})$aryl and —C(O)CH$R_{AA}$$NH_2$; wherein $R_{AA}$ is a side chain selected from a proteinogenic amino acid;

$R_{6'}$ is selected from H, azido, cyano, $(C_1\text{-}C_8)$alkyl, $(C_1\text{-}C_8)$thio-alkyl, $(C_1\text{-}C_8)$heteroalkyl and OR; wherein R is selected from H and $(C_1\text{-}C_8)$alkyl;

$R_{8'}$ is selected from H, OR, $NR_{15'}$—$R_{16'}$, NH—NH$R_{15'}$, SH, CN, $N_3$ and halogen; wherein R is selected from H and $(C_1\text{-}C_8)$alkyl, and $R_{15'}$ and $R_{16'}$ are independently selected from H, $(C_1\text{-}C_8)$alkyl and $(C_1\text{-}C_8)$alkyl-$(C_5\text{-}C_{12})$aryl and —CH$R_{AA'}$$CO_2$H wherein $R_{AA'}$ is a side chain selected from a proteinogenic or non-proteinogenic amino acid;

Y' is selected from CH, $CH_2$, $CHCH_3$, $C(CH_3)_2$ and $CCH_3$;

n is an integer selected from 1 to 3;

- - - represents the point of attachment;

$\overline{---}$ represents a single or double bond depending on Y'; and

∿∿ represents the alpha or beta anomer depending on the position of $R_{1'}$;

$R_8$ is select from H, OR, $NR_{15}R_{16}$, NH—NH$R_{15}$, SH, CN, $N_3$ and halogen; wherein R is selected from H and $(C_1\text{-}C_8)$alkyl, and $R_{15}$ and $R_{16}$ are independently selected from H, $(C_1\text{-}C_8)$alkyl and $(C_1\text{-}C_8)$alkyl-$(C_5\text{-}C_{12})$aryl —CH$R_{AA}$$CO_2$H wherein $R_{AA}$ is a side chain selected from a proteinogenic or non-proteinogenic amino acid;

Y is selected from CH, $CH_2$, $CHCH_3$, $C(CH_3)_2$ and $CCH_3$;

$\overline{---}$ represents a single or double bond depending on Y; and

∿∿ represents the alpha or beta anomer depending on the position of $R_1$, for use in the treatment of an antineoplastic-induced toxicity, preferably wherein the toxicity is selected from cardiotoxicity, nephrotoxicity, neurotoxicity, haematotoxicity, hepatotoxicity, lymphoid toxicity, gastrointestinal toxicity, dermal toxicity, ototoxicity, reproductive toxicity, bone toxicity, genetic toxicity and bladder toxicity; more preferably wherein the toxicity is selected from cardiotoxicity, nephrotoxicity, haematotoxicity, hepatotoxicity, lymphoid toxicity, gastrointestinal toxicity, dermal toxicity, reproductive toxicity, bone toxicity, genetic toxicity and bladder toxicity.

According to one embodiment, X represents an oxygen.

According to one embodiment, $R_1$ and $R_6$ are identical and represent hydrogen.

According to one embodiment, $R_3$ and $R_4$ are identical and represent hydrogen.

According to one embodiment, $R_2$ and $R_5$ are identical and represent OH.

According to one embodiment, Y is selected from CH and $CH_2$.

According to one embodiment, $R_7$ is selected from H, $P(O)R_9R_{10}$ and

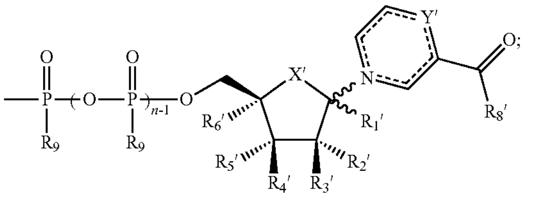

wherein $R_9$ and $R_{10}$ are as described herein above;

X' is an oxygen;

$R_{1'}$ and $R_{6'}$ each represents a hydrogen;

$R_{2'}$, $R_{3'}$, $R_{4'}$ and $R_{5'}$ are independently selected from hydrogen and OH;

$R_{8'}$ is $NH_2$;

Y' is selected from CH and $CH_2$;

n is equal to 2;

- - - represents the point of attachment;

--- represents a single or double bond depending on Y'; and

∿∿∿ represents the alpha or beta anomer depending on the position of $R_{1'}$.

According to one embodiment, $R_8$ is $NH_2$.

According to one embodiment, the compound for use according to the invention is selected from compounds 001 to 014:

| Compounds (anomers) | Structure |
|---|---|
| 001 (beta) | 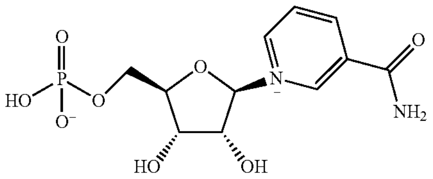 |
| 002 (alpha) | 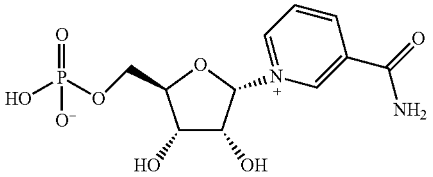 |
| 003 (beta) | 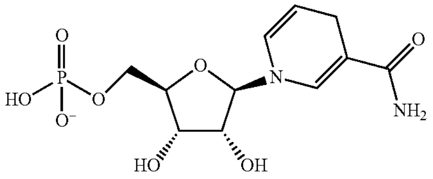 [SMILES: NC(=O)C1=CN([C@@H]2O[C@H](COP(=O)([O-])O)[C@@H](O)[C@H]2O)C=CC1] |
| 004 (alpha) | 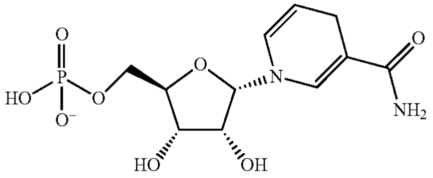 [SMILES: NC(=O)C1=CN([C@H]2O[C@H](COP(=O)([O-])O)[C@@H](O)[C@H]2O)C=CC1] |
| 005 (beta) | 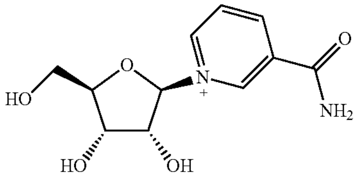 |
| 006 (alpha) | 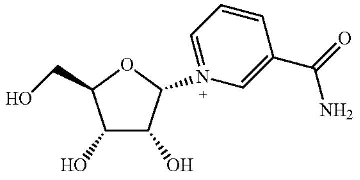 |

-continued
| Compounds (anomers) | Structure |
|---|---|
| 007 (beta) | 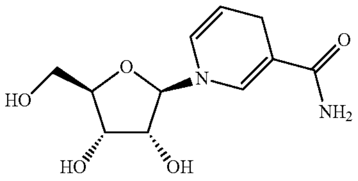 [SMILES: NC(=O)C1=CN([C@@H]2O[C@H](CO)[C@@H](O)[C@H]2O)C=CC1] |
| 008 (alpha) | 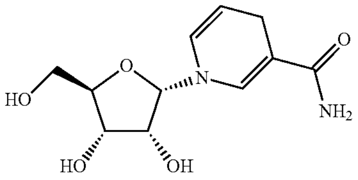 [SMILES: NC(=O)C1=CN([C@H]2O[C@H](CO)[C@@H](O)[C@H]2O)C=CC1] |
| 009 (beta, beta) | 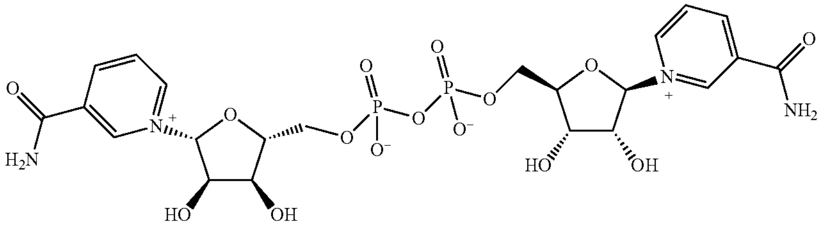 |
| 010 (beta, alpha) | 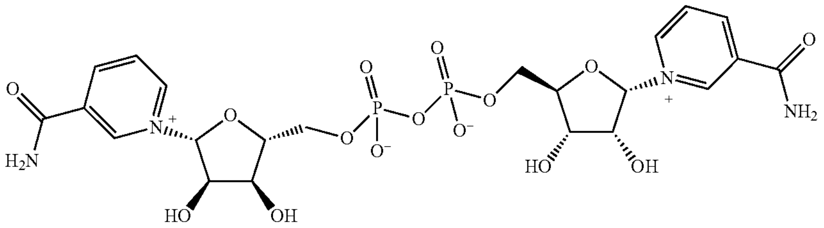 |
| 011 (alpha, alpha) | 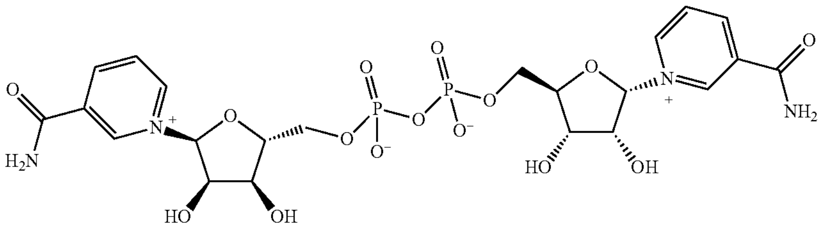 |
| 012 (beta, beta) | 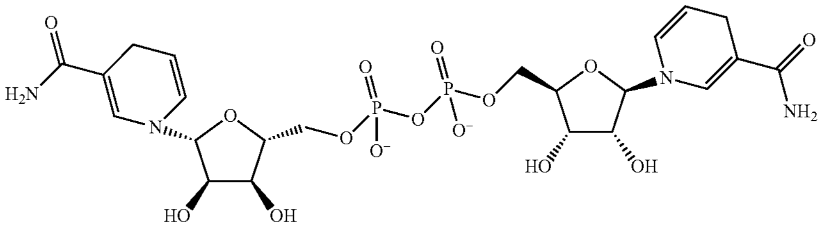 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |
| 013 (beta, alpha) | 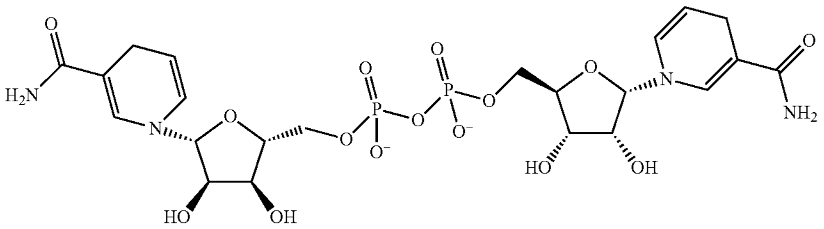 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |

-continued

| Compounds (anomers) | Structure |
|---|---|
| 014 (alpha, alpha) | 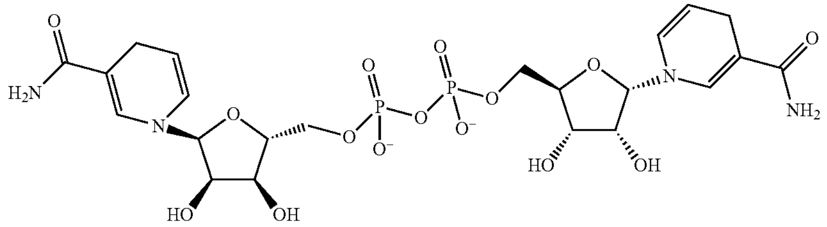 [SMILES: NC(=O)C1=CN([C@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |

and pharmaceutically acceptable salts and solvates thereof.

According to one embodiment, the toxicity is induced by an antineoplastic agent selected from anthracyclines, alkylating agents, taxanes, antimetabolites, Biologic Response Modifiers, Histone Deacetylase Inhibitors, Hormonal Agents, vinca alkaloids, topoisomerase inhibitors, monoclonal antibodies, tyrosine kinase inhibitors and a mixture thereof.

According to one embodiment, the toxicity is induced by an anthracycline selected from doxorubicin, daunorubicin, epirubicin, idarubicin, bleomycin, mitomycin, mitoxantrone, plicamycin and valrubicin.

According to one embodiment, the toxicity is induced by doxorubicin.

According to one embodiment, the toxicity is a cardiotoxicity selected from heart failure, left ventricular failure, myocardial ischemia, myocardial infarction, QT prolongation, torsade de pointes, arrhythmias, pericarditis, myocarditis, bradycardia, hypertension and thromboembolism.

The invention also relates to a pharmaceutical composition for use in the treatment of a toxicity, comprising at least one compound for use according to the invention and at least one pharmaceutically acceptable carrier.

According to one embodiment, the pharmaceutical composition for use comprises in addition to at least one compound for use as described herein above, at least one active ingredient selected from a natural extract; antineoplastic agents; antidepressant; antiretroviral; beta blockers; antidiabetic; diuretics; antihypertensive; antiarrhythmic; CNS stimulant; antimalarial; immunosuppressant; antifungal; cytokines; interferon; anabolic-androgenic steroids; adrenergic stimulants; neuromodulator; COX inhibitor; angiotensin-converting enzyme inhibitors; angiotensin receptor blockers; ranolazine; metformin; mineralocorticoid receptor antagonists; hydroxymethylglutaryl-coenzyme A reductase inhibitors; antioxidants such as self-nanoemulsifying formulation of quercetin; Q10 coenzyme; vitamin E; L-carnitine; steroids; cyclosporine; mycophenolate mofetil; Anti-TNF such as Infliximab or Etanercept; Anti-Il1 such as Sraninka; Anti-PGF such as Gleevec; Anti-CD20 such as Rituximab; Maltol; PTEN modulators; Nobiletin; pyrroloquinoline quinone; urolithine.

BRIEF DESCRIPTION OF THE DRAWINGS

FIG. 1 is a histogram showing the survival rate of mice 5 days after DOX (20 mg/kg) or vehicle induction, with and without treatments. ##$p<0.01$: Fisher's test Dox mice treated with vehicle vs control mice, £$p<0.05$, ££$p<0.01$: Fisher's test Dox mice treated with vehicle vs Dox mice treated with NMN analogs.

FIGS. 2 (A and B) shows the bodyweight evolution of mice treated and a histogram showing the bodyweight (BW) gain calculated. A shows the bodyweight evolution of mice treated ith compound 001, 010 and 011 (180 mg/kg) or vehicle, before (light gray symbol) and 5 days after saline solution or DOX (20 mg/kg) injection (dark gray symbol). £££ $p<0.001$: Two-way ANOVA followed by Bonferroni post-test body weight before Dox injection vs 5 days after Dox injection. B is a histogram showing the bodyweight (BW) gain calculated as follow: BW at the day of sacrifice minus BW before injection of mice treated with compound 001, 010 and 011 (180 mg/kg) or vehicle, with and without DOX (20 mg/kg) injection. *** $p<0.001$: Mann-Whitney test Dox mice treated with vehicle vs control mice, $$p<0.01, $$$p<0.001 One-way ANOVA followed by post-hoc Dunnett test Dox mice treated with vehicle n vs Dox mice treated with NMN analogs.

FIGS. 3 (A, B and C) includes three histograms showing left ventricle (LV) end diastolic (A) and end systolic volumes (B) and ejection fraction (C) 5 days after saline solution or DOX (20 mg/kg) injection.  $p<0.01$, * $p<0.001$: Mann-Whitney test Dox mice treated with vehicle vs control mice, $p<0.05, $$$p<0.001 Kruskal-Wallis test followed by post-hoc Dunn test Dox mice treated with vehicle vs Dox mice treated with NMN analogs.

FIGS. 4 (A, B, C and D) includes four histograms showing LV end diastolic and end systolic diameters (A and B respectively), fractional shortening (C) and heart rate (D) 5 days after saline solution or DOX (20 mg/kg) injection.  $p<0.01$,  $p<0.001$: t-test or Mann-Whitney test Dox mice treated with vehicle vs control mice, $$$p<0.001: One-way ANOVA followed by post-hoc Dunnett test or Kruskal-Wallis test followed by post-hoc Dunn Dox mice treated with vehicle vs Dox mice treated with NMN analogs (180 mg/kg) or vehicle.

FIGS. 5 (A, B, C and D) includes four histograms showing LV anterior wall thickness in systole and in diastole (A and B respectively) and posterior wall thickness in systole and in diastole (C and D respectively) 5 days after saline solution or DOX (20 mg/kg) injection. *$p<0.05$, ** $p<0.01$: Mann-Whitney test Dox mice treated with vehicle vs control mice.

FIGS. 6 (A and B) includes two histograms showing heart weight (A) and heart weight normalized to tibial length (B) 5 days after saline solution or DOX (20 mg/kg) injection. *** $p<0.001$: t-test Dox mice treated with vehicle vs control mice.

FIGS. 7 (A and B) includes two histograms showing LDH concentrations (U/L, A) and LDH (fold change, B) in the plasma of mice 5 days after saline solution or DOX (20 mg/kg) injection. ** $p<0.01$: Mann-Whitney test Dox mice treated with vehicle vs control mice; $p<0.05: Kruskal-Wallis test Dox mice treated with vehicle vs Dox mice treated with NMN analogs (180 mg/kg) or vehicle.

DETAILED DESCRIPTION

The definitions and explanations below are for the terms as used throughout the entire application, including both the specification and the claims.

When describing the compounds of the invention, the terms used are to be construed in accordance with the following definitions, unless indicated otherwise.

Unless indicated otherwise, the nomenclature of substituents that are not explicitly defined herein are arrived at by naming the adjacent functionality toward the point of attachment followed by the terminal portion of the functionality. For example, the substituent "arylalkyl" refers to the group-(aryl)-(alkyl).

In the present invention, the following terms have the following meanings:

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 12 carbon atoms, preferably from 1 to 10 carbon atoms, preferably from 1 to 8 carbon atoms, more preferably from 1 to 6 carbon atoms, still more preferably 1 to 2 carbon atoms. Alkyl groups may be linear or branched. Suitable alkyl groups include methyl, ethyl, n-propyl, i-propyl, n-butyl, i-butyl, s-butyl and t-butyl, pentyl and its isomers (e.g. n-pentyl, iso-pentyl), hexyl and its isomers (e.g. n-hexyl, isohexyl), heptyl and its isomers (e.g. n-heptyl, iso-heptyl), octyl and its isomers (e.g. n-octyl, iso-octyl), nonyl and its isomers (e.g. n-nonyl, iso-nonyl), decyl and its isomers (e.g. n-decyl, iso-decyl), undecyl and its isomers, dodecyl and its isomers. Preferred alkyl groups include methyl, ethyl, n-propyl, i-propyl, n-butyl, i-butyl, s-butyl, t-butyl, n-pentyl, n-hexyl, n-heptyl, n-octyl, n-nonyl and n-decyl. Saturated branched alkyls include, without being limited to, i-propyl, s-butyl, i-butyl, t-butyl, i-pentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl.

Cx-Cy-alkyl refers to alkyl groups which comprise x to y carbon atoms.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

The term "alkenyl" as used herein refers to an unsaturated hydrocarbyl group, which may be linear or branched, comprising one or more carbon-carbon double bonds. Suitable alkenyl groups comprise between 2 and 12 carbon atoms, preferably between 2 and 8 carbon atoms, still more preferably between 2 and 6 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkynyl" as used herein refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Non limiting examples of alkynyl groups are ethynyl, 2-propynyl, 2-butynyl, 3-butynyl, 2-pentynyl and its isomers, 2-hexynyl and its isomers- and the like.

The term "alkoxy" as used herein refers to any group —O-alkyl, wherein alkyl is as defined above. Suitable alkoxy groups include for example methoxy, ethoxy, n-propoxy, isopropoxy, n-butoxy, t-butoxy, sec-butoxy, and n-pentoxy.

The term "amino add" as used herein refers to an alpha-aminated carboxylic acid, i.e. a molecule comprising a carboxylic acid functional group and an amine functional group in alpha position of the carboxylic acid group, for example a proteinogenic amino acid or a non-proteinogenic amino acid.

The term "aryl" as used herein refers to a polyunsaturated, aromatic hydrocarbyl group having a single ring (i.e. phenyl) or multiple aromatic rings fused together (e.g. naphthyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenyl, biphenylenyl, 5- or 6-tetralinyl, naphthalen-1- or -2-yl, 4-, 5-, 6- or 7-indenyl, 1- 2-, 3-, 4- or 5-acenaphthylenyl, 3-, 4- or 5-acenaphthenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "cycloalkyl" as used herein is a cyclic alkyl, alkenyl or alkynyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

The term "halo" or "halogen" means fluoro, chloro, bromo, or iodo. Preferred halo groups are fluoro and chloro.

The term "haloalkyl", alone or as part of another group, refers to an alkyl radical having the meaning as defined above wherein one or more hydrogen atoms are replaced with a halogen as defined above. Non-limiting examples of such haloalkyl radicals include chloromethyl, 1-bromoethyl, fluoromethyl, difluoromethyl, trifluoro methyl, 1,1,1-trifluoroethyl and the like. $C_x$-$C_y$-haloalkyl are haloalkyl groups which comprise x to y carbon atoms. Preferred haloalkyl groups are difluoromethyl and trifluoromethyl.

The term "heteroalkyl" means an alkyl group as defined above in which one or more carbon atoms are replaced by a heteroatom selected from oxygen, nitrogen and sulfur atoms. In heteroalkyl groups, the heteroatoms are linked along the alkyl chain only to carbon atoms, i.e. each heteroatom is separated from any other heteroatom by at least one carbon atom. However, the nitrogen and sulphur heteroatoms may optionally be oxidized and the nitrogen heteroatoms may optionally be quaternized. A heteroalkyl is bonded to another group or molecule only through a carbon atom, i.e. the bonding atom is not selected from the heteroatoms included in the heteroalkyl group.

Where at least one carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo [2,1-b][1,3]thiazolyl, thieno[3,2-b]furanyl, thieno[3,2-b] thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.

Where at least one carbon atom in a cycloalkyl group is replaced with a heteroatom, the resultant ring is referred to herein as "heterocyloalkyl" or "heterocyclyl".

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

The term "hydroxyalkyl" refers to an alkyl radical having the meaning as defined above wherein one or more hydrogen atoms are replaced with —OH moieties.

The term "thio-alkyl" refers to an alkyl radical having the meaning as defined above wherein one or more hydrogen atoms are replaced with —SH moieties.

The term "non-proteinogenic amino acid" as used herein refers to an amino acid not naturally encoded or found in the genetic code of living organism. Non limiting examples of non-proteinogenic amino acid are ornithine, citrulline, argininosuccinate, homoserine, homocysteine, cysteine-sulfinic acid, 2-aminomuconic acid, δ-aminolevulinic acid, β-alanine, cystathionine, γ-aminobutyrate, DOPA, 5-hydroxytryptophan, D-serine, ibotenic acid, α-aminobutyrate, 2-aminoisobutyrate, D-leucine, D-valine, D-alanine or D-glutamate.

The term "proteinogenic amino acid" as used herein refers to an amino acid that is incorporated into proteins during translation of messenger RNA by ribosomes in living organisms, i.e. Alanine (ALA), Arginine (ARG), Asparagine (ASN), Aspartate (ASP), Cysteine (CYS), Glutamate (glutamic acid) (GLU), Glutamine (GLN), Glycine (GLY), Histidine (HIS), Isoleucine (ILE), Leucine (LEU), Lysine (LYS), Methionine (MET), Phenylalanine (PHE), Proline (PRO), Pyrrolysine (PYL), Selenocysteine (SEL), Serine (SER), Threonine (THR), Tryptophan (TRP), Tyrosine (TYR) or Valine (VAL).

The term "prodrug" as used herein means the pharmacologically acceptable derivatives of compounds of Formula (I) such as esters whose in vivo biotransformation product is the active drug. Prodrugs are characterized by increased bio-availability and are readily metabolized into the active compounds in vivo. Suitable prodrugs for the purpose of the invention include phosphoramidates, HepDirect, (S)-acyl-2-thioethyl (SATE), carboxylic esters, in particular alkyl esters, aryl esters, acyloxyalkyl esters, and dioxolene carboxylic esters; ascorbic acid esters.

The term "substituent" or "substituted" means that a hydrogen radical on a compound or group is replaced by any desired group which is substantially stable under the reaction conditions in an unprotected form or when protected by a protecting group. Examples of preferred substituents include, without being limited to, halogen (chloro, iodo, bromo, or fluoro); alkyl; alkenyl; alkynyl, as described above; hydroxy; alkoxy; nitro; thiol; thioether, imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary);

$CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an arylalkyl, a heteroarylalkyl, a haloalkyl, —$C(O)NR_{17}R_{18}$, —$NR_{19}C(O)R_{20}$, a halo, —$OR_{19}$, cyano, nitro, a haloalkoxy, —$C(O)R_{19}$, —$NR_{17}R_{18}$, —$SR_{19}$, —$C(O)OR_{19}$, —$OC(O)R_{19}$, —$NR_{19}C(O)NR_{17}R_{18}$, —$OC(O)NR_{17}R_{18}$, —$NR_{19}C(O)OR_{20}$, —$S(O)_rR_{19}$, —$NR_{19}S(O)_rR_{20}$, —$OS(O)_rR_{20}$, $S(O)_rNR_{17}R_{18}$, —O, —S, and —N—$R_{19}$, wherein r is 1 or 2; $R_{17}$ and $R_{18}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted arylalkyl, or an optionally substituted heteroarylalkyl; or $R_{17}$ and $R_{18}$ taken together with the nitrogen to which they are attached is optionally substituted heterocycloalkyl or optionally substituted heteroaryl; and $R_{19}$ and $R_{20}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted arylalkyl, or an optionally substituted heteroarylalkyl. In certain embodiments, the term "substituent" or the adjective "substituted" refers to a solubilizing group.

The bonds of an asymmetric carbon can be represented here using a solid triangle ( ), a dashed triangle ( ) or a zigzag line ( ).

The term "active ingredient" refers to a molecule or a substance whose administration to a subject slows down or stops the progression, aggravation, or deterioration of one or more symptoms of a disease, or condition; alleviates the symptoms of a disease or condition; cures a disease or condition. According to one embodiment, the therapeutic ingredient is a small molecule, either natural or synthetic. According to another embodiment, the therapeutic ingredient is a biological molecule such as for example an oligonucleotide, a siRNA, a miRNA, a DNA fragment, an aptamer, an antibody and the like.

The term "administration", or a variant thereof (e.g., "administering"), means providing the active agent or active ingredient, alone or as part of a pharmaceutically acceptable composition, to the patient in whom/which the condition, symptom, or disease is to be treated.

The term "drug" refers to any substance that causes a change in physiology or psychology of a subject when administrated to the subject. In the context of the invention, "drug" encompasses both drugs for medical use ("medicinal drug" or "active ingredient") and drugs for non-medical use, e.g., recreational drugs (e.g., psychoactive drugs).

By "pharmaceutically acceptable" it is meant that the ingredients of a pharmaceutical composition are compatible with each other and not deleterious to the patient.

The terms "pharmaceutically acceptable excipient", "pharmaceutically acceptable carrier" or "pharmaceutical vehicle" refer to an inert medium or carrier used as a solvent or diluent in which the pharmaceutically active ingredient is formulated and/or administered, and which does not produce an adverse, allergic or other reaction when administered to an animal, preferably a human being. This includes all solvents, dispersion media, coatings, antibacterial and antifungal agents, isotonic agents, absorption retardants and other similar ingredients. For human administration, preparations must meet standards of sterility, general safety and purity as required by regulatory agencies such as the FDA or EMA. For the purposes of the invention, "pharmaceutically acceptable excipient" includes all pharmaceutically acceptable excipients as well as all pharmaceutically acceptable carriers, diluents, and/or adjuvants.

The term "pharmaceutically acceptable salts" includes the acid addition and base salts. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminum, arginine, benzathine, calcium, choline, diethylamine, 2-(diethylamino)ethanol, diolamine, ethanolamine, glycine, 4-(2-hydroxyethyl)-morpholine, lysine, magnesium, meglumine, morpholine, olamine, potassium, sodium, tromethamine and zinc salts.

Hemisalts of acids and bases may also be formed, for example, hemisulphate and hemicalcium salts.

Pharmaceutically acceptable salts of compounds of Formula (I) may be prepared by one or more of these methods:

(i) by reacting the compound of Formula (I) with the desired acid;

(ii) by reacting the compound of Formula (I) with the desired base;

(iii) by removing an acid- or base-labile protecting group from a suitable precursor of the compound of Formula (I) or by ring-opening a suitable cyclic precursor, e.g., a lactone or lactam, using the desired acid; and/or (iv) by converting one salt of the compound of Formula (I) to another by reaction with an appropriate acid or by means of a suitable ion exchange column.

All these reactions are typically carried out in solution. The salt may precipitate from solution and be collected by filtration or may be recovered by evaporation of the solvent. The degree of ionization in the salt may vary from completely ionized to almost non-ionized.

Although generally, with respect to the salts of the compounds of the invention, pharmaceutically acceptable salts are preferred, it should be noted that the invention in its broadest sense also includes non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula (I).

The term "solvate" is used herein to describe a molecular complex comprising a compound of the invention and containing stoichiometric or sub-stoichiometric amounts of one or more pharmaceutically acceptable solvent molecule, such as ethanol. The term 'hydrate' refers to a solvate when said solvent is water.

The term "human" refers to a subject of both genders and at any stage of development (i.e., neonate, infant, juvenile, adolescent, adult).

The term "subject" refers to a mammal, preferably a human. According to the present invention, a subject is a mammal, preferably a human, suffering from an antineoplastic-induced toxicity and/or that is susceptible to develop an antineoplastic-induced toxicity. In one embodiment, the subject is a "patient", i.e., a mammal, preferably a human, who/which is awaiting the receipt of, or is receiving medical care or was/is/will be the object of a medical procedure or is monitored for the development of an antineoplastic-induced toxicity.

The term "therapeutically effective amount" (or more simply an "effective amount") as used herein refers to the amount of active agent or active ingredient that is aimed at, without causing significant negative or adverse side effects to the subject in need of treatment, preventing, reducing, alleviating or slowing down (lessening) one or more of the symptoms of antineoplastic-induced toxicities.

The terms "treat", "treating" or "treatment", as used herein, refer to a therapeutic treatment, to a prophylactic (or preventative) treatment, or to both a therapeutic treatment and a prophylactic (or preventive) treatment, wherein the object is to prevent, reduce, alleviate, and/or slow down (lessen) one or more of the symptoms of a drug-induced toxicity, especially an antineoplastic-induced toxicity, in a subject in need thereof. In one embodiment, "treating" or "treatment" refers to a therapeutic treatment. In another embodiment, "treating" or "treatment" refers to a prophylactic or preventive treatment. In yet another embodiment, "treating" or "treatment" refers to both a prophylactic (or preventive) treatment and a therapeutic treatment.

The term "toxicity" refers to a condition that result in damage to the organism such as cardiotoxicity, nephrotoxicity, neurotoxicity, haematotoxicity, hepatotoxicity, lymphoid toxicity, gastrointestinal toxicity, dermal toxicity, metabolic toxicity, ototoxicity, reproductive toxicity, bone toxicity, genetic toxicity and bladder toxicity. According to the invention, the toxicity may for example be caused by the direct or indirect effect of a molecule or a substance on an organ, tissue or system such as a drug, alcohol or heavy metals. The toxicity may for example also be caused by at least one disease or disorder.

The term "cardiotoxicity" refers to a condition that result in damage to the heart muscle, such as heart failure, left ventricular failure, myocardial ischemia, myocardial infarction, QT prolongation, torsade de pointes, arrhythmias, pericarditis, myocarditis, bradycardia, hypertension and thromboembolism. According to the invention, the cardiotoxicity may for example be caused by the direct or indirect effect of a molecule or a substance on the heart, such as a drug, alcohol or heavy metals. The cardiotoxicity may for example also be caused by at least one disease or disorder. If severe, cardiotoxicity may lead to cardiomyopathy.

The present invention thus relates to the use of nicotinamide mononucleotide derivatives for the treatment of an antineoplastic-induced toxicity, wherein the toxicity is preferably selected from cardiotoxicity, nephrotoxicity, haematotoxicity, hepatotoxicity, lymphoid toxicity, gastrointestinal toxicity, dermal toxicity, reproductive toxicity, bone toxicity, genetic toxicity and bladder toxicity. In particular, the present invention relates to nicotinamide mononucleotide derivatives for use in the treatment of an antineoplastic-induced toxicity, in a subject in need thereof.

Nicotinamide Mononucleotide Derivatives

In one embodiment, the nicotinamide mononucleotide derivative of the present invention is a compound of Formula (I)

(I)

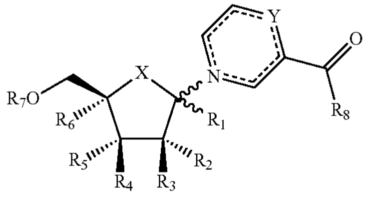

or a pharmaceutically acceptable salt or solvate thereof; wherein:

X is selected from O, $CH_2$, S, Se, CHF, $CF_2$ and $C{=}CH_2$;

$R_1$ is selected from H, azido, cyano, $(C_1\text{-}C_8)$alkyl, $(C_1\text{-}C_8)$thio-alkyl, $(C_1\text{-}C_8)$heteroalkyl and OR; wherein R is selected from H and $(C_1\text{-}C_8)$alkyl;

$R_2$, $R_3$, $R_4$ and $R_5$ are independently selected from H, halogen, azido, cyano, hydroxyl, $(C_1\text{-}C_{12})$alkyl, $(C_1\text{-}C_{12})$thio-alkyl, $(C_1\text{-}C_{12})$heteroalkyl, $(C_1\text{-}C_{12})$haloalkyl and OR; wherein R is selected from H, $(C_1\text{-}C_{12})$alkyl, —$C(O)(C_1\text{-}C_{12})$alkyl, —$C(O)NH(C_1\text{-}C_{12})$alkyl, —$C(O)O(C_1\text{-}C_{12})$alkyl, —C(O)aryl, —$C(O)(C_1\text{-}C_{12})$alkyl-$(C_5\text{-}C_{12})$aryl, —$C(O)NH(C_1\text{-}C_{12})$alkyl-$(C_5\text{-}C_{12})$aryl, —$C(O)O(C_1\text{-}C_{12})$alkyl-$(C_5\text{-}C_{12})$aryl and —$C(O)CHR_{AA}NH_2$; wherein $R_{AA}$ is a side chain selected from a proteinogenic amino acid;

$R_6$ is selected from H, azido, cyano, $(C_1\text{-}C_8)$alkyl, $(C_1\text{-}C_8)$thio-alkyl, $(C_1\text{-}C_8)$heteroalkyl and OR; wherein R is selected from H and $(C_1\text{-}C_8)$alkyl;

$R_7$ is selected from H, $P(O)R_9R_{10}$, $P(S)R_9R_{10}$ and

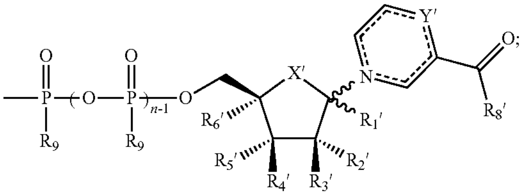

wherein:

$R_9$ and $R_{10}$ are independently selected from OH, $OR_{11}$, $NR_{13}R_{14}$, $(C_1\text{-}C_8)$alkyl, $(C_2\text{-}C_8)$alkenyl, $(C_2\text{-}C_8)$alkynyl, $(C_3\text{-}C_{10})$cycloalkyl, $(C_5\text{-}C_{12})$aryl, $(C_5\text{-}C_{12})$aryl-$(C_1\text{-}C_8)$alkyl, $(C_1\text{-}C_8)$alkyl-$(C_5\text{-}C_{12})$aryl, $(C_1\text{-}C_8)$heteroalkyl, $(C_3\text{-}C_8)$heterocycloalkyl, $(C_5\text{-}C_{12})$heteroaryl and $NHCR_\alpha R_{\alpha'}C(O)OR_{12}$; wherein:

$R_{11}$ is selected from $(C_1\text{-}C_{10})$alkyl, $(C_3\text{-}C_{10})$cycloalkyl, $(C_5\text{-}C_{12})$aryl, $(C_1\text{-}C_{10})$alkyl-$(C_5\text{-}C_{12})$aryl, substituted $(C_5\text{-}C_{12})$aryl, $(C_1\text{-}C_{10})$heteroalkyl, $(C_1\text{-}C_{10})$haloalkyl, —$(CH_2)_mC(O)(C_1\text{-}C_{15})$alkyl, —$(CH_2)_mOC(O)(C_1\text{-}C_{15})$alkyl, —$(CH_2)_mOC(O)O(C_1\text{-}C_{15})$alkyl, —$(CH_2)_mSC(O)(C_1\text{-}C_{15})$alkyl, —$(CH_2)_mC(O)O(C_1\text{-}C_{15})$alkyl, —$(CH_2)_mC(O)O(C_1\text{-}C_{15})$alkyl-$(C_5\text{-}C_{12})$aryl; wherein m is an integer selected from 1 to 8; and —P(O)(OH)OP(O)(OH)$_2$; and an internal or external counterion;

$R_{12}$ is selected from hydrogen, $(C_1-C_{10})$alkyl, $(C_2-C_8)$alkenyl, $(C_2-C_8)$alkynyl, $(C_1-C_{10})$haloalkyl, $(C_3-C_{10})$cycloalkyl, $(C_3-C_{10})$heterocycloalkyl, $(C_5-C_{12})$aryl, $(C_1-C_4)$alkyl-$(C_5-C_{12})$aryl and $(C_5-C_{12})$heteroaryl; wherein said aryl or heteroaryl groups are optionally substituted by one or two groups selected from halogen, trifluoromethyl, $(C_1-C_6)$alkyl, $(C_1-C_6)$alkoxy and cyano;

$R_{13}$ and $R_{14}$ are independently selected from H, $(C_1-C_8)$alkyl and $(C_1-C_8)$alkyl-$(C_5-C_{12})$aryl; and $R_\alpha$ and $R_{\alpha'}$ are independently selected from an hydrogen, $(C_1-C_{10})$alkyl, $(C_2-C_{10})$alkenyl, $(C_2-C_{10})$alkynyl, $(C_3-C_{10})$cycloalkyl, $(C_1-C_{10})$thio-alkyl, $(C_1-C_{10})$hydroxyalkyl, $(C_1-C_{10})$alkyl-$(C_5-C_{12})$aryl, $(C_5-C_{12})$aryl, —$(CH_2)_3$NHC(=NH)NH$_2$, (1H-indol-3-yl)methyl, (1H-imidazol-4-yl)methyl and a side chain selected from a proteinogenic or non-proteinogenic amino acid; wherein said aryl groups are optionally substituted with a group selected from hydroxyl, $(C_1-C_{10})$alkyl, $(C_1-C_6)$alkoxy, halogen, nitro and cyano; or $R_9$ and $R_{10}$ together with the phosphorus atom to which they are attached form a 6-membered ring wherein —$R_9$-$R_{10}$— represents —O—$CH_2$—$CH_2$—CHR—O—; wherein R is selected from hydrogen, $(C_5-C_6)$aryl and $(C_5-C_6)$heteroaryl; wherein said aryl or heteroaryl groups are optionally substituted by one or two groups selected from halogen, trifluoromethyl, $(C_1-C_6)$alkyl, $(C_1-C_6)$alkoxy and cyano;

X' is selected from O, $CH_2$, S, Se, CHF, $CF_2$ and C=$CH_2$;

$R_{1'}$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_{2'}$, $R_{3'}$, $R_{4'}$ and $R_{5'}$ are independently selected from H, halogen, azido, cyano, hydroxyl, $(C_1-C_{12})$alkyl, $(C_1-C_{12})$thio-alkyl, $(C_1-C_{12})$heteroalkyl, $(C_1-C_{12})$haloalkyl and OR; wherein R is selected from H, $(C_1-C_{12})$alkyl, —C(O)$(C_1-C_{12})$alkyl, —C(O)NH$(C_1-C_{12})$alkyl, —C(O)O$(C_1-C_{12})$alkyl, —C(O)aryl, —C(O)$(C_1-C_{12})$alkyl-$(C_5-C_{12})$aryl, —C(O)NH$(C_1-C_{12})$alkyl-$(C_5-C_{12})$aryl, —C(O)O$(C_1-C_{12})$alkyl-$(C_5-C_{12})$aryl and —C(O)CHR$_{AA}$NH$_2$; wherein $R_{AA}$ is a side chain selected from a proteinogenic amino acid;

$R_{6'}$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_{8'}$ is selected from H, OR, NR$_{15'}$R$_{16'}$, NH—NHR$_{15'}$, SH, CN, $N_3$ and halogen; wherein R is selected from H and $(C_1-C_8)$alkyl, and $R_{15'}$ and $R_{16'}$ are independently selected from H, $(C_1-C_8)$alkyl and $(C_1-C_8)$alkyl-$(C_5-C_{12})$aryl and —CHR$_{AA'}$CO$_2$H wherein $R_{AA'}$ is a side chain selected from a proteinogenic or non-proteinogenic amino acid;

Y' is selected from CH, $CH_2$, $CHCH_3$, $C(CH_3)_2$ and $CCH_3$;

n is an integer selected from 1 to 3;

- - - represents the point of attachment;

represents a single or double bond depending on Y'; and represents the alpha or beta anomer depending on the position of $R_{1'}$;

$R_8$ is selected from H, OR, NR$_{15}$R$_{16}$, NH—NHR$_{15}$, SH, CN, $N_3$ and halogen; wherein R is selected from H and $(C_1-C_8)$alkyl, and $R_{15}$ and $R_{16}$ are independently selected from H, $(C_1-C_8)$alkyl, $(C_1-C_8)$alkyl-aryl and —CHR$_{AA}$CO$_2$H wherein $R_{AA}$ is a side chain selected from a proteinogenic or non-proteinogenic amino acid;

Y is selected from CH, $CH_2$, $CHCH_3$, $C(CH_3)_2$ and $CCH_3$;

represents a single or double bond depending on Y; and represents the alpha or beta anomer depending on the position of $R_1$.

In one embodiment, in Formula (I):

X is selected from O, $CH_2$, S, Se, CHF, $CF_2$ and C=$CH_2$;

$R_1$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_2$, $R_3$, $R_4$ and $R_5$ are independently selected from H, halogen, azido, cyano, hydroxyl, $(C_1-C_{12})$alkyl, $(C_1-C_{12})$thio-alkyl, $(C_1-C_{12})$heteroalkyl, $(C_1-C_{12})$haloalkyl and OR; wherein R is selected from H, $(C_1-C_{12})$alkyl, —C(O)$(C_1-C_{12})$alkyl, —C(O)NH$(C_1-C_{12})$alkyl, —C(O)O$(C_1-C_{12})$alkyl, —C(O)aryl, —C(O)$(C_1-C_{12})$alkyl aryl, —C(O)NH$(C_1-C_{12})$alkyl-$(C_5-C_{12})$aryl, —C(O)O$(C_1-C_{12})$alkyl-$(C_5-C_{12})$aryl and —C(O)CHR$_{AA}$NH$_2$; wherein $R_{AA}$ is a side chain selected from a proteinogenic amino acid;

$R_6$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_7$ is selected from H, P(O)$R_9R_{10}$, P(S)$R_9R_{10}$ and

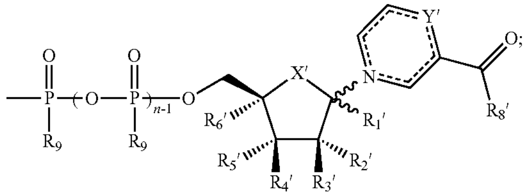

herein:

$R_9$ and $R_{10}$ are independently selected from OH, OR$_{11}$, NHR$_{13}$, NR$_{13}$R$_{14}$, $(C_1-C_8)$alkyl, $(C_2-C_8)$alkenyl, $(C_2-C_8)$alkynyl, $(C_3-C_{10})$cycloalkyl, $(C_5-C_{12})$aryl, $(C_5-C_{12})$aryl-$(C_1-C_8)$alkyl, $(C_1-C_8)$alkyl-$(C_5-C_{12})$aryl, $(C_1-C_8)$heteroalkyl, $(C_3-C_8)$heterocycloalkyl, $(C_5-C_{12})$heteroaryl and NHCR$_\alpha$R$_{\alpha'}$C(O)R$_{12}$; wherein:

$R_{11}$ is selected from $(C_1-C_{10})$alkyl, $(C_3-C_{10})$cycloalkyl, $(C_5-C_{12})$aryl, $(C_1-C_{10})$alkyl-$(C_5-C_{12})$aryl, substituted $(C_5-C_{12})$aryl, $(C_1-C_{10})$heteroalkyl, $(C_1-C_{10})$haloalkyl, —$(CH_2)_m$C(O)$(C_1-C_{15})$alkyl, —$(CH_2)_m$OC(O)$(C_1-C_{15})$alkyl, —$(CH_2)_m$OC(O)O$(C_1-C_{15})$alkyl, —$(CH_2)_m$SC(O)$(C_1-C_{15})$alkyl, —$(CH_2)_m$C(O)O$(C_1-C_{15})$alkyl, —$(CH_2)_m$C(O)O$(C_1-C_{15})$alkyl aryl; wherein m is an integer selected from 1 to 8; and —P(O)(OH)OP(O)(OH)$_2$; an internal or external counterion;

$R_{12}$ is selected from hydrogen, $(C_1-C_{10})$alkyl, $(C_2-C_8)$alkenyl, $(C_2-C_8)$alkynyl, $(C_1-C_{10})$haloalkyl, $(C_3-C_{10})$cycloalkyl, $(C_3-C_{10})$cycloheteroalkyl, $(C_5-C_{12})$aryl, $(C_1-C_4)$alkyl-$(C_5-C_{12})$aryl and $(C_5-$ $C_{12}$)heteroaryl; wherein said aryl or heteroaryl groups are optionally substituted by one or two groups selected from halogen, trifluoromethyl, ($C_1$-$C_6$)alkyl, ($C_1$-$C_6$)alkoxy and cyano;

$R_{13}$ and $R_{14}$ are independently selected from H, ($C_1$-$C_8$)alkyl and ($C_1$-$C_8$)alkyl-($C_5$-$C_{12}$)aryl;

$R_\alpha$ and $R_{\alpha'}$ are independently selected from an hydrogen, ($C_1$-$C_{10}$)alkyl, ($C_2$-$C_{10}$)alkenyl, ($C_2$-$C_{10}$)alkynyl, ($C_3$-$C_{10}$)cycloalkyl, ($C_1$-$C_{10}$)thio-alkyl, ($C_1$-$C_{10}$)hydroxylalkyl, ($C_1$-$C_{10}$)alkyl-($C_5$-$C_{12}$)aryl, ($C_5$-$C_{12}$)aryl, —$(CH_2)_3$NHC(=NH)$NH_2$, (1H-indol-3-yl)methyl, (1H-imidazol-4-yl)methyl and a side chain selected from a proteinogenic or non-proteinogenic amino acid; wherein said aryl groups are optionally substituted with a group selected from hydroxyl, $C_1$-$C_{10}$ alkyl, $C_1$-$C_6$ alkoxy, halogen, nitro and cyano; or $R_9$ and $R_{10}$ together with the phosphorus atoms to which they are attached form a 6-membered ring wherein —$R_9$-$R_{10}$-represents —$CH_2$—$CH_2$—CHR— or —O—$CH_2$—$CH_2$—CHR—O—; wherein R is selected from hydrogen, ($C_5$-$C_6$)aryl and ($C_5$-$C_6$)heteroaryl; wherein said aryl or heteroaryl groups are optionally substituted by one or two groups selected from halogen, trifluoromethyl, ($C_1$-$C_6$)alkyl, ($C_1$-$C_6$)alkoxy and cyano;

X' is selected from O, $CH_2$, S, Se, CHF, $CF_2$ and C=$CH_2$;

$R_{1'}$ is selected from H, azido, cyano, ($C_1$-$C_8$)alkyl, ($C_1$-$C_8$)thio-alkyl, ($C_1$-$C_8$)heteroalkyl and OR; wherein R is selected from H and ($C_1$-$C_8$)alkyl;

$R_{2'}$, $R_{3'}$, $R_{4'}$ and $R_{5'}$ are independently selected from H, halogen, azido, cyano, hydroxyl, ($C_1$-$C_{12}$)alkyl, ($C_1$-$C_{12}$)thio-alkyl, ($C_1$-$C_{12}$)heteroalkyl, ($C_1$-$C_{12}$)haloalkyl and OR; wherein R is selected from H, ($C_1$-$C_{12}$)alkyl, —C(O)($C_1$-$C_{12}$)alkyl, —C(O)NH($C_1$-$C_{12}$)alkyl, —C(O)O($C_1$-$C_{12}$)alkyl, —C(O)aryl, —C(O)($C_1$-$C_{12}$)alkyl aryl, —C(O)NH($C_1$-$C_{12}$)alkyl-($C_5$-$C_{12}$)aryl, —C(O)O($C_1$-$C_{12}$)alkyl-($C_5$-$C_{12}$)aryl and —C(O)CH$R_{AA}$$NH_2$; wherein $R_{AA}$ is a side chain selected from a proteinogenic amino acid;

$R_{6'}$ is selected from H, azido, cyano, ($C_1$-$C_8$)alkyl, ($C_1$-$C_8$)thio-alkyl, ($C_1$-$C_8$)heteroalkyl and OR; wherein R is selected from H and ($C_1$-$C_8$)alkyl;

$R_{8'}$ is selected from H, OR, $NHR_{15'}$, $NR_{15'}R_{16'}$, NH—$NHR_{15'}$, SH, CN, $N_3$ and halogen; wherein $R_{15'}$ and $R_{16'}$ are independently selected from H, ($C_1$-$C_8$)alkyl and ($C_1$-$C_8$)alkyl-aryl;

Y' is selected from CH, $CH_2$, $C(CH_3)_2$ and $CCH_3$;

n is an integer selected from 1 to 3;

---- represents a single or double bond according to Y'; and

∿∿ represents the alpha or beta anomer depending on the position of $R_{1'}$;

$R_8$ is selected from H, OR, $NHR_{15}$, $NR_{15}R_{16}$, NH—$NHR_{15}$, SH, CN, $N_3$ and halogen; wherein $R_{15}$ and $R_{16}$ are independently selected from H, $C_1$-$C_8$ alkyl and $C_1$-$C_8$ alkyl-aryl;

Y is selected from CH, $CH_2$, $C(CH_3)_2$ and $CCH_3$;

---- represents single or double bond according to Y; and

∿∿ represents the alpha or beta anomer depending on the position of $R_1$.

The nicotinamide mononucleotide derivatives of the invention may comprise one or more charged atoms. Particularly, when present, the phosphate groups may bear one or more charge, preferably one or more negative charge. Moreover, the nitrogen atom of the pyridine part of the nicotinamide group may bear one positive charge when it is quaternized. The presence of one or more charged atom in the nicotinamide mononucleotide derivatives of the invention depends on the conditions, especially pH conditions, that one skilled in the art will recognize.

According to one embodiment, X is selected from O, $CH_2$ and S. In one embodiment, X is oxygen.

According to one embodiment, $R_1$ is selected from hydrogen and OH. In one embodiment, $R_1$ is hydrogen. In one embodiment, $R_1$ is OH.

According to one embodiment, $R_2$, $R_3$, $R_4$ and $R_5$ are independently selected from hydrogen, halogen, hydroxyl, $C_1$-$C_{12}$ alkyl and OR; wherein R is as described herein above. In a preferred embodiment, $R_2$, $R_3$, $R_4$ and $R_5$ are independently selected from hydrogen, hydroxyl and OR; wherein R is as described herein above. In a more preferred embodiment $R_2$, $R_3$, $R_4$ and $R_5$ are independently selected from hydrogen and OH.

According to one embodiment, $R_2$ and $R_3$ are identical. In one embodiment, $R_2$ and $R_3$ are identical and represent OH. In one embodiment, $R_2$ and $R_3$ are identical and represent hydrogen.

According to one embodiment, $R_2$ and $R_3$ are different. In a preferred embodiment, $R_2$ is hydrogen and $R_3$ is OH. In a more preferred embodiment, $R_2$ is OH and $R_3$ is hydrogen.

According to one embodiment, $R_4$ and $R_5$ are identical. In one embodiment, $R_4$ and $R_5$ are identical and represent OH. In one embodiment, $R_4$ and $R_5$ are identical and represent hydrogen.

According to one embodiment, $R_4$ and $R_5$ are different. In a preferred embodiment, $R_4$ is OH and $R_5$ is hydrogen. In a more preferred embodiment, $R_4$ is hydrogen and $R_5$ is OH.

According to one embodiment, $R_3$ and $R_4$ are different. In one embodiment, $R_3$ is OH and $R_4$ is hydrogen. In one embodiment, $R_3$ is hydrogen and $R_4$ is OH.

According to one embodiment, $R_3$ and $R_4$ are identical. In a preferred embodiment, $R_3$ and $R_4$ are identical and represent OH. In a more preferred embodiment, $R_3$ and $R_4$ are identical and represent hydrogen.

According to one embodiment, $R_2$ and $R_5$ are different. In one embodiment, $R_2$ is hydrogen and $R_5$ is OH. In one embodiment, $R_2$ is OH and $R_5$ is hydrogen.

According to one embodiment, $R_2$ and $R_5$ are identical. In a preferred embodiment, $R_2$ and $R_5$ are identical and represent hydrogen. In a more preferred embodiment, $R_2$ and $R_5$ are identical and represent OH.

According to one embodiment, $R_6$ is selected from hydrogen and OH. In one embodiment, $R_6$ is OH. In a preferred embodiment, $R_6$ is hydrogen.

According to one embodiment, $R_1$ and $R_6$ are each independently selected from hydrogen and OH. According to one embodiment, $R_1$ and $R_6$ are both hydrogen atoms.

According to one embodiment, $R_7$ is selected from hydrogen, $P(O)R_9R_{10}$ and

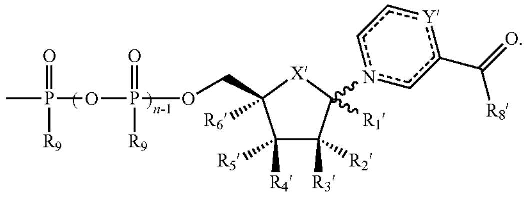

According to one embodiment, $R_7$ is hydrogen.

According to one embodiment, $R_7$ is $P(O)R_9R_{10}$; wherein $R_9$ and $R_{10}$ are as described herein above. In a preferred embodiment, $R_7$ is $P(O)(OH)_2$.

According to one embodiment, $R_7$ is

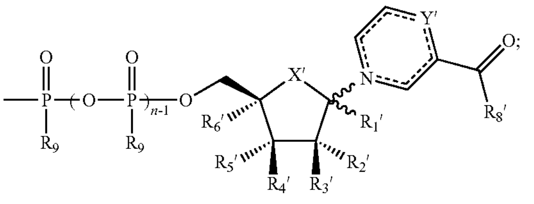

wherein $R_{1'}$, $R_{2'}$, $R_{3'}$, $R_{4'}$, $R_{5'}$, $R_{6'}$, $R_{7'}$, $R_{8'}$, $R_{9'}$, X', Y', n, - - -, $\overline{---}$ and $\sim\sim$ are as described herein above for compounds of Formula (I).

According to a preferred embodiment, $R_7$ is

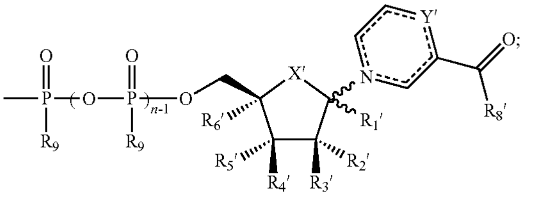

wherein:

X' is selected from O, $CH_2$ and S, preferably X' is O;

$R_{1'}$ is selected from hydrogen and OH, preferably $R_{1'}$ is hydrogen;

$R_{2'}$, $R_{3'}$, $R_{4'}$ and $R_{5'}$ are independently selected from hydrogen, halogen, hydroxyl, $(C_1-C_{12})$alkyl and OR; wherein R is as described herein above, preferably $R_{2'}$, $R_{3'}$, $R_{4'}$ and $R_{5'}$ are independently selected from hydrogen, hydroxyl and OR; wherein R is as described herein above, more preferably $R_{2'}$, $R_{3'}$, $R_{4'}$ and $R_{5'}$ are independently selected from hydrogen and OH;

$R_{6'}$ is selected from hydrogen and OH, preferably $R_{6'}$ is hydrogen;

$R_{8'}$ is selected from H, OR and $NR_{15'}R_{16'}$; wherein $R_{15'}$ and $R_{16'}$ are as described herein above, preferably $R_{8'}$ is $NHR_{15'}$; wherein $R_{15'}$ is as described herein above, more preferably $R_{8'}$ is $NH_2$;

Y' is selected from CH and $CH_2$;

n is an integer selected from 1 to 3;

- - - represents the point of attachment;

$\overline{---}$ represent a single or double bond depending on Y'; and $\sim\sim$ represents the alpha or beta anomer depending on the position of $R_{1'}$.

According to one embodiment, in Formula (I), $R_7$ is

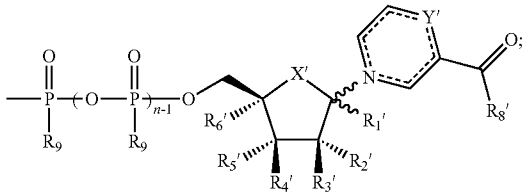

X and X' are independently selected from O, $CH_2$ and S, preferably X and X' are O;

$R_1$ and $R_{1'}$ are independently selected from hydrogen and OH, preferably $R_1$ and $R_{1'}$ are hydrogen;

$R_2$, $R_3$, $R_4$, $R_5$, $R_{2'}$, $R_{3'}$, $R_{4'}$ and $R_{5'}$ are independently selected from hydrogen, halogen, hydroxyl, $(C_1-C_{12})$ alkyl and OR; wherein R is as described herein above, preferably $R_2$, $R_3$, $R_4$, $R_5$, $R_{2'}$, $R_{3'}$, $R_{4'}$ and $R_{5'}$ are independently selected from hydrogen, hydroxyl and OR; wherein R is as described herein above, more preferably $R_2$, $R_3$, $R_4$, $R_5$, $R_{2'}$, $R_{3'}$, $R_{4'}$ and $R_{5'}$ are independently selected from hydrogen and OH;

$R_6$ and $R_{6'}$ are independently selected from hydrogen and OH, preferably $R_6$ and $R_{6'}$ are hydrogen;

$R_8$ and $R_{8'}$ are independently selected from H, OR and $NR_{15'}R_{16'}$; wherein $R_{15'}$ and $R_{16'}$ are as described herein above, preferably $R_8$ and $R_{8'}$ are $NHR_{15'}$; wherein $R_{15'}$ is as described herein above, more preferably $R_8$ and $R_{8'}$ are $NH_2$;

Y and Y' are independently selected from CH and $CH_2$;

n is an integer selected from 1 to 3;

- - - represents the point of attachment;

$\overline{---}$ represents a single or double bond depending on Y and Y'; and $\sim\sim$ represents the alpha or beta anomers depending on the position of $R_1$ and $R_{1'}$.

According to one embodiment, n is 1. According to one embodiment, n is 2. According to one embodiment, n is 3.

According to one embodiment, $R_8$ is selected from H, OR and $NR_{15}R_{16}$; wherein $R_{15}$ and $R_{16}$ are as described herein above. In a preferred embodiment, $R_8$ is $NHR_{15}$; wherein $R_{15}$ is as described herein above. In one embodiment, $R_8$ is $NH_2$.

According to one embodiment, Y is a CH or $CH_2$. In one embodiment, Y is a CH. In one embodiment, Y is a $CH_2$.

According to a preferred embodiment, the nicotinamide mononucleotide derivative used in the present invention is of general Formula (II):

(II)

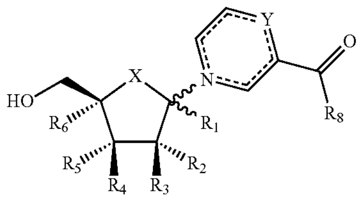

or a pharmaceutically acceptable salt or solvate thereof; wherein $R_1$, $R_2$, $R_3$, $R_4$, $R_5$, $R_6$, $R_8$, X, Y, $\overline{---}$ and $\sim\sim$ are as described herein above for compounds of Formula (I).

According to one embodiment, preferred compounds of general Formula (II) are those of Formula (II-1):

(II-1)

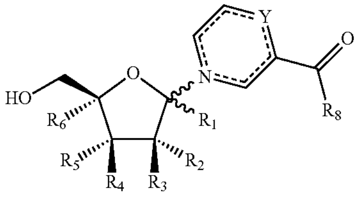

or a pharmaceutically acceptable salt or solvate thereof; wherein $R_1$, $R_2$, $R_3$, $R_4$, $R_5$, $R_6$, $R_8$, Y, = and ~ are as described herein above for compounds of Formula (I).

According to one embodiment, preferred compounds of general Formula (II) are those of Formula (II-2):

(II-2)

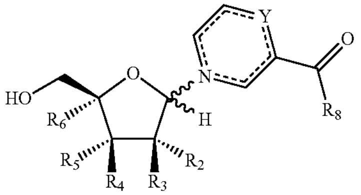

or a pharmaceutically acceptable salt or solvate thereof; wherein $R_2$, $R_3$, $R_4$, $R_5$, $R_6$, $R_8$, Y, = and ~ are as described herein above for compounds of Formula (I).

According to one embodiment, preferred compounds of general Formula (II) are those of Formula (II-3):

(II-3)

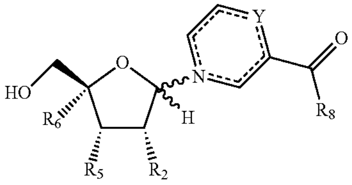

or a pharmaceutically acceptable salt or solvate thereof; wherein $R_2$, $R_5$, $R_6$, $R_8$, Y, = and ~ are as described herein above for compounds of Formula (I).

According to one embodiment, preferred compounds of general Formula (II) are those of Formula (II-4):

(II-4)

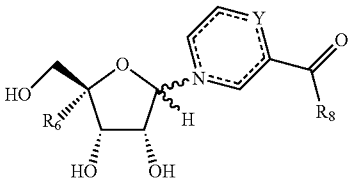

or a pharmaceutically acceptable salt or solvate thereof; wherein $R_6$, $R_8$, Y, = and ~ are as described herein above for compounds of Formula (I).

According to one embodiment, preferred compounds of general Formula (II) are those of Formula (II-5):

(II-5)

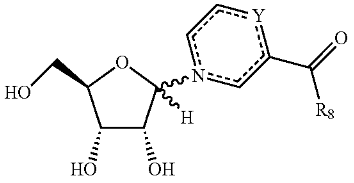

or a pharmaceutically acceptable salt or solvate thereof; wherein $R_8$, Y, = and ~ are as described herein above for compounds of Formula (I).

According to one embodiment, preferred compounds of general Formula (II) are those of Formula (II-6):

(II-6)

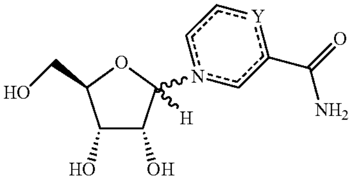

or a pharmaceutically acceptable salt or solvate thereof; wherein Y, = and ~ are as described herein above for compounds of Formula (I).

According to one embodiment, preferred compounds of general Formula (II) are those of Formula (II-7):

(II-7)

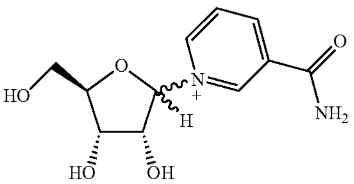

or a pharmaceutically acceptable salt or solvate thereof; wherein ~ is as described herein above for compounds of Formula (I).

According to a preferred embodiment, the invention relates to compounds of general Formula (II-8):

(II-8)

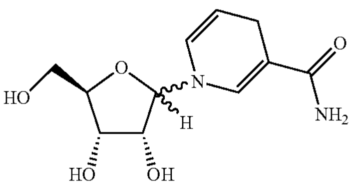

or a pharmaceutically acceptable salt or solvate thereof; wherein ~ is as described herein above for compounds of Formula (I).

According to another preferred embodiment, the nicotinamide mononucleotide derivative used in the present invention is of general Formula (III):

(III)

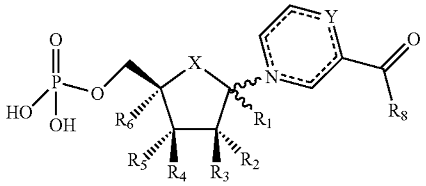

or a pharmaceutically acceptable salt or solvate thereof; wherein $R_1$, $R_2$, $R_3$, $R_4$, $R_5$, $R_6$, $R_8$, X, Y, --- and ~~~ as described herein above for compounds of Formula (I).

According to one embodiment, preferred compounds of general Formula (III) are those of Formula (III-1):

(III-1)

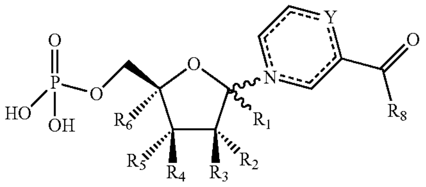

or a pharmaceutically a malt or solvate thereof; wherein $R_1$, $R_2$, $R_3$, $R_4$, $R_5$, $R_6$, $R_8$, Y, --- and ~~~ are as described herein above for compounds of Formula (I).

According to one embodiment, preferred compounds of general Formula (III) are those of Formula (III-2):

(III-2)

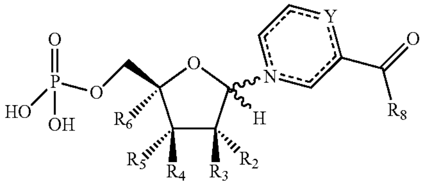

or a pharmaceutically acceptable salt or solvate thereof; wherein $R_2$, $R_3$, $R_4$, $R_5$, $R_6$, $R_8$, Y, --- and ~~~ are as described herein above for compounds of Formula (I).

According to one embodiment, preferred compounds of general Formula (III) are those of Formula (III-3):

(III-3)

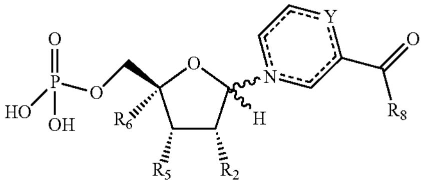

or a pharmaceutically acceptable salt or solvate thereof; wherein $R_2$, $R_5$, $R_6$, $R_8$, Y, --- and ~~~ are as described herein above for compounds of Formula (I).

According to one embodiment, preferred compounds of general Formula (III) are those of Formula (III-4):

(III-4)

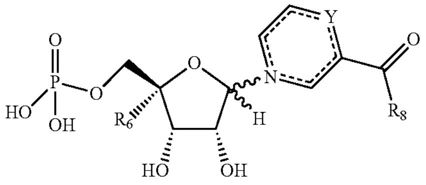

or a pharmaceutically acceptable salt or solvate thereof; wherein $R_6$, $R_8$, Y, --- and ~~~ are as described herein above for compounds of Formula (I).

According to one embodiment, preferred compounds of general Formula (III) are those of Formula (III-5):

(III-5)

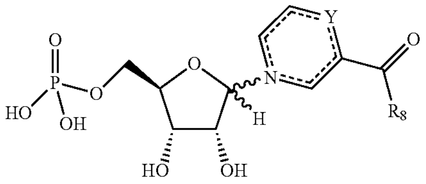

or a pharmaceutically acceptable salt or solvate thereof; wherein $R_8$, Y, --- and ~~~ are as described herein above for compounds of Formula (I).

According to one embodiment, preferred compounds of general Formula (III) are those of Formula (III-6):

(III-6)

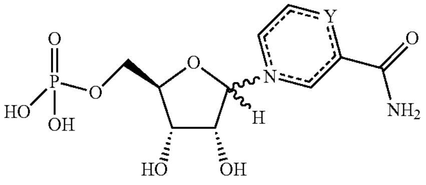

or a pharmaceutically acceptable salt or solvate thereof; wherein Y, --- and ~~~ are as described herein above for compounds of Formula (I).

According to one embodiment, preferred compounds of general Formula (III) are those of Formula (III-7):

(III-7)

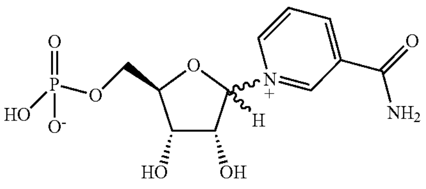

or a pharmaceutically acceptable salt or solvate thereof; wherein ~~~ is as described herein above for compounds of Formula (I).

According to one embodiment, preferred compounds of general Formula (III) are those of Formula (III-8):

(III-8)

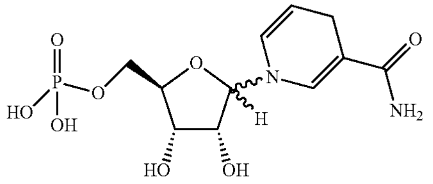

or a pharmaceutically acceptable salt or solvate thereof; wherein ∿∿ is as described herein above for compounds of Formula (I).

According to another preferred embodiment, the nicotinamide mononucleotide derivative used in the present invention is of general Formula (IV):

(IV)

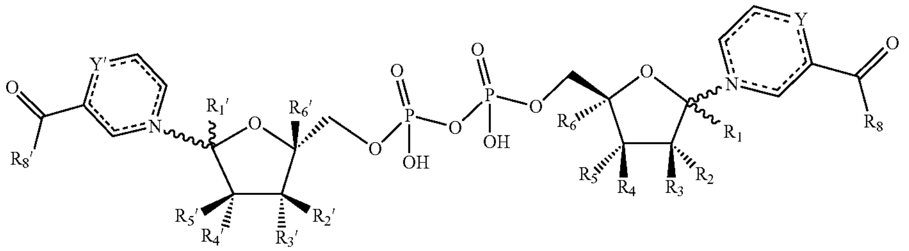

or a pharmaceutically acceptable salt or solvate thereof; wherein $R_1$, $R_{1'}$, $R_2$, $R_{2'}$, $R_3$, $R_{3'}$, $R_4$, $R_{4'}$, $R_5$, $R_{5'}$, $R_6$, $R_{6'}$, $R_8$, $R_{8'}$, X, X', Y, Y', ⎓ and ∿∿ are as described herein above for compounds of Formula (I).

According to one embodiment, preferred compounds of general Formula (IV) are those of Formula (IV-1):

(IV-1)

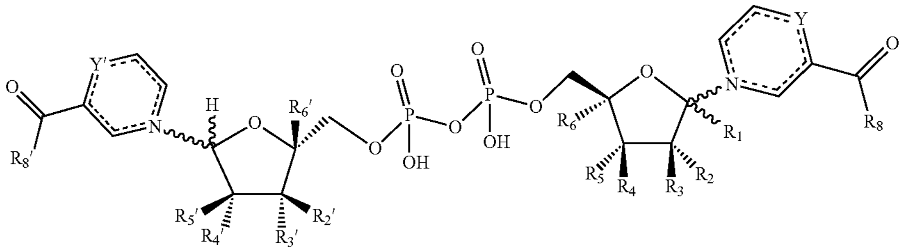

or a pharmaceutically acceptable salt or solvate thereof; wherein $R_1$, $R_{1'}$, $R_2$, $R_{2'}$, $R_3$, $R_{3'}$, $R_4$, $R_{4'}$, $R_5$, $R_{5'}$, $R_6$, $R_{6'}$, $R_8$, $R_{8'}$, Y, Y', ⎓ and ∿∿ are as described herein above for compounds of Formula (I).

According to one embodiment, preferred compounds of general Formula (IV) are those of Formula (IV-2):

(IV-2)

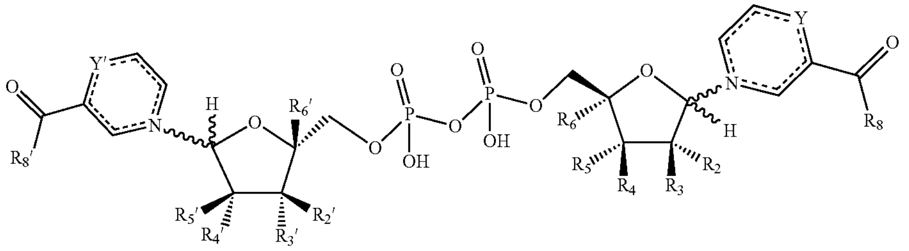

or a pharmaceutically acceptable salt or solvate thereof; wherein $R_2$, $R_{2'}$, $R_3$, $R_{3'}$, $R_4$, $R_{4'}$, $R_5$, $R_{5'}$, $R_6$, $R_{6'}$, $R_8$, $R_{8'}$, Y, Y', ⎓ and ∿∿∿ are as described herein above for compounds of Formula (I).

According to one embodiment, preferred compounds of general Formula (IV) are those of Formula (IV-3):

(IV-3)

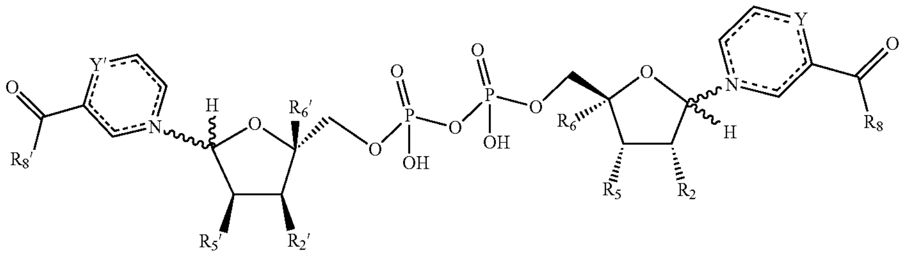

or a pharmaceutically acceptable salt or solvate thereof; wherein $R_2$, $R_{2'}$, $R_5$, $R_{5'}$, $R_6$, $R_{6'}$, $R_8$, $R_{8'}$, Y, Y', ⎓ and ∿∿∿ are as described herein above for compounds of Formula (I).

According to one embodiment, preferred compounds of general Formula (IV) are those of Formula (IV-4):

(IV-4)

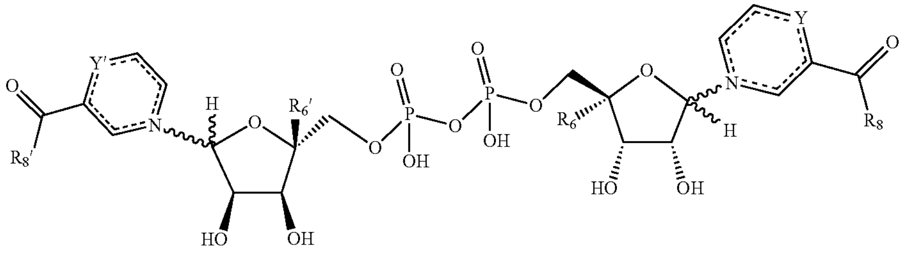

or a pharmaceutically acceptable salt or solvate thereof; wherein $R_6$, $R_{6'}$, $R_8$, $R_{8'}$, Y, Y', ⎓ and ∿∿∿ are as described herein above for compounds of Formula (I).

According to one embodiment, preferred compounds of general Formula (IV) are those of Formula (IV-5):

(IV-5)

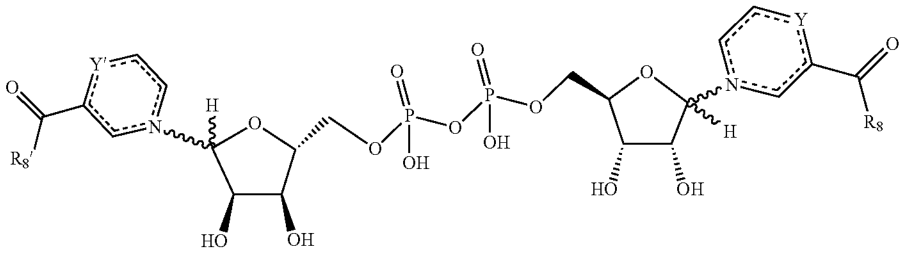

or a pharmaceutically acceptable salt or solvate thereof; wherein $R_6$, $R_{6'}$, $R_8$, $R_{8'}$, Y, Y', ⎓ and ∿∿∿ are as described herein above for compounds of Formula (I).

According to one embodiment, preferred compounds of general Formula (IV) are those of Formula (IV-6):

(IV-6)

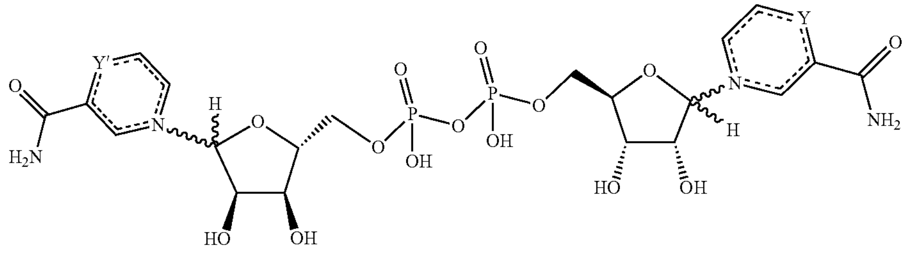

or a pharmaceutically acceptable salt or solvate thereof; wherein Y, Y', ⎓ and ∿∿ are as described herein above for compounds of Formula (I).

According to one embodiment, preferred compounds of general Formula (IV) are those of Formula (IV-7):

(IV-7)

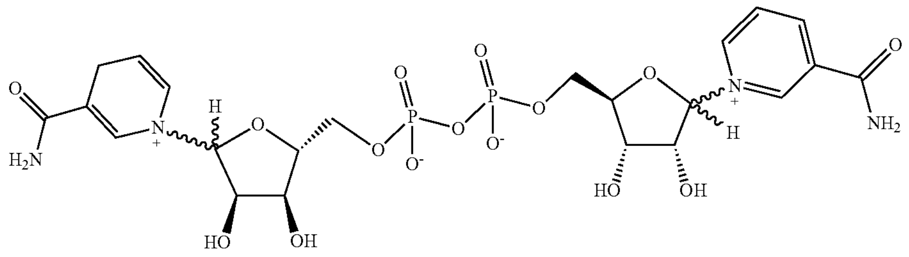

or a pharmaceutically acceptable salt or solvate thereof; wherein ∿∿ is as described herein above for compounds of Formula (I).

According to one embodiment, preferred compounds of general Formula (IV) are those of Formula (IV-8):

(IV-8)

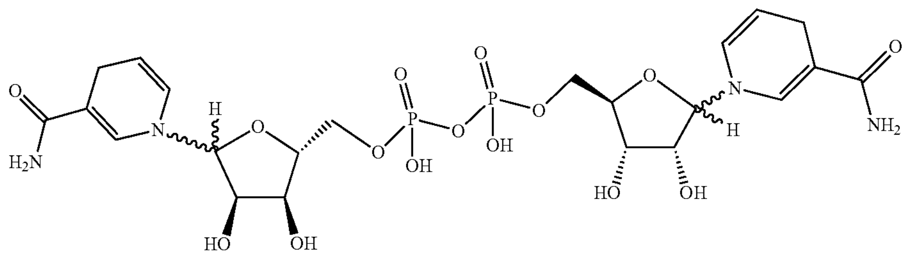

or a pharmaceutically acceptable salt or solvate thereof; wherein ∿∿ is as described herein above for compounds of Formula (I).

According to one embodiment, the nicotinamide mononucleotide derivative used in the present invention is selected from compounds 001 to 014 from Table 1 below and pharmaceutically acceptable salts and solvates thereof:

TABLE 1
| Compounds (anomers) | Structure |
|---|---|
| 001 (beta) NMN | 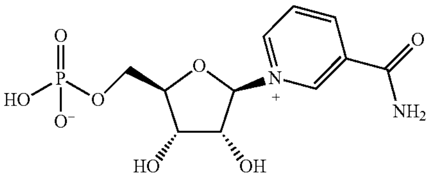 |
| 002 (alpha) | 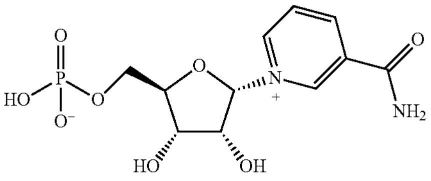 |
| 003 (beta) | 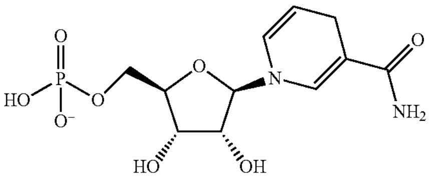 [SMILES: NC(=O)C1=CN([C@@H]2O[C@H](COP(=O)([O-])O)[C@@H](O)[C@H]2O)C=CC1] |
| 004 (alpha) | 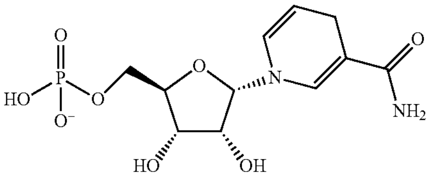 [SMILES: NC(=O)C1=CN([C@H]2O[C@H](COP(=O)([O-])O)[C@@H](O)[C@H]2O)C=CC1] |
| 005 (beta) | 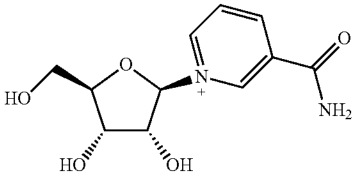 |
| 006 (alpha) | 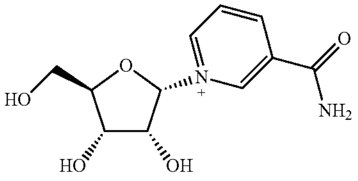 |
| 007 (beta) | 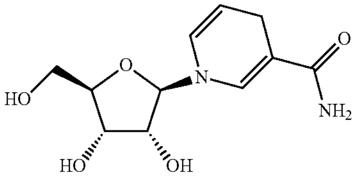 [SMILES: NC(=O)C1=CN([C@@H]2O[C@H](CO)[C@@H](O)[C@H]2O)C=CC1] |
| 008 (alpha) | 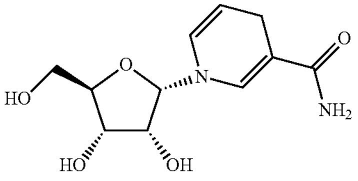 [SMILES: NC(=O)C1=CN([C@H]2O[C@H](CO)[C@@H](O)[C@H]2O)C=CC1] |

TABLE 1-continued
| Compounds (anomers) | Structure |
| --- | --- |
| 009 (beta, beta) | 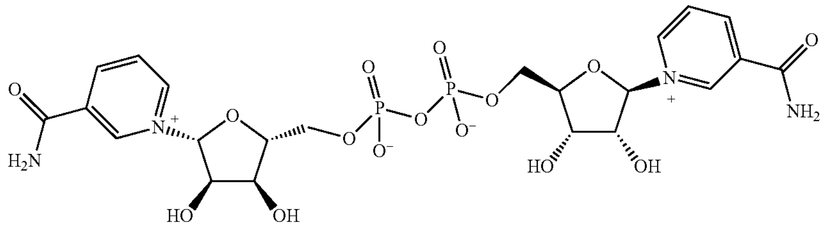 |
| 010 (beta, alpha) | 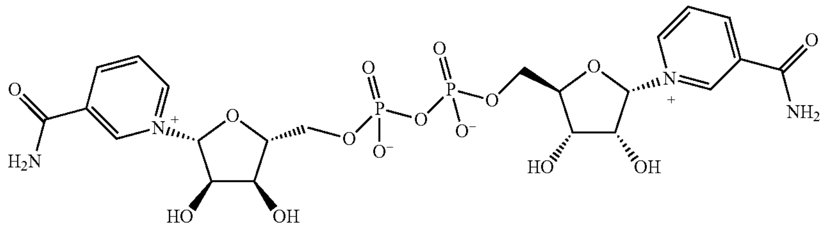 |
| 011 (alpha, alpha) | 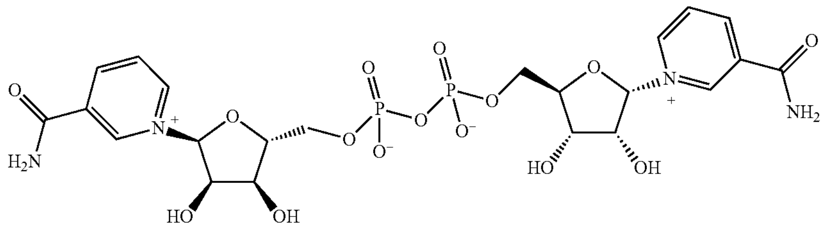 |
| 012 (beta, beta) | 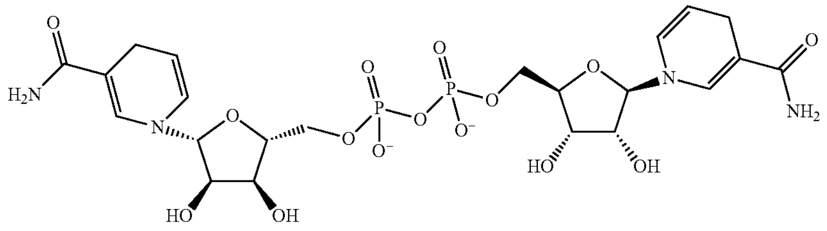 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |
| 013 (beta, alpha) | 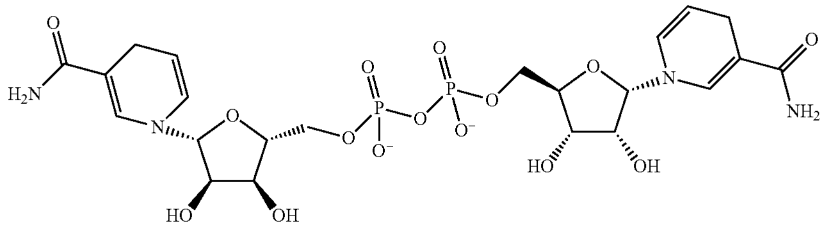 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| 014 (alpha, alpha) | 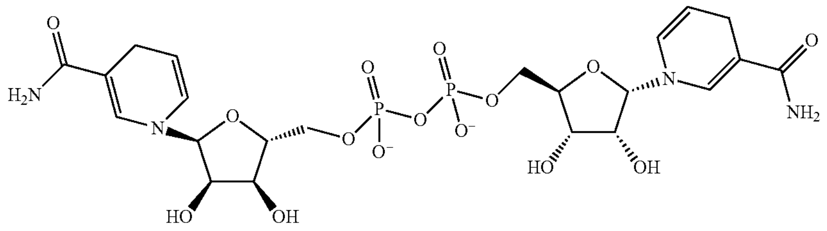 [SMILES: NC(=O)C1=CN([C@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |

According to one embodiment, preferred nicotinamide mononucleotide derivatives are compounds 001 to 014 or a pharmaceutically acceptable salt or solvate thereof.

According to one embodiment, more preferred nicotinamide mononucleotide derivatives are compounds 001, 002, 009, 010 and 011 or a pharmaceutically acceptable salt or solvate thereof.

According to one embodiment, more preferred nicotinamide mononucleotide derivatives are compounds 001 and 002 or a pharmaceutically acceptable salt or solvate thereof.

According to another embodiment, more preferred nicotinamide mononucleotide derivatives are compounds 009, 010 and 011 or a pharmaceutically acceptable salt or solvate thereof.

According to one embodiment, even more preferred nicotinamide mononucleotide derivatives are compounds 002, 010 and 011 or a pharmaceutically acceptable salt or solvate thereof.

All references to compounds of Formula (I) and subformulae thereof include references to salts, solvates, multi-component complexes, liquid crystals thereof. All references to compounds of Formula (I) and subformulae thereof include references to polymorphs and crystal habits thereof.

All references to compounds of Formula (I) and subformulae thereof include references to pharmaceutically acceptable prodrugs thereof.

The nicotinamide mononucleotide derivatives used in the present invention can be under the form of a pharmaceutical composition. In one embodiment, the pharmaceutical composition comprises a nicotinamide mononucleotide derivative as defined hereinabove, and at least one pharmaceutically acceptable carrier.

Process

According to another aspect, the invention relates to a method for the preparation of the compound of Formula (I) as described hereinabove.

In particular, the compounds of Formula (I) may be prepared as described below from substrates A-E. It shall be understood by a person skilled in the art that these schemes are in no way limiting and that variations may be made without departing from the spirit and scope of this invention.

According to one embodiment, the method involves in a first step the mono-phosphorylation of a compound of Formula (A), in the presence of phosphoryl chloride and a trialkyl phosphate, to yield the phosphorodichloridate of Formula (B):

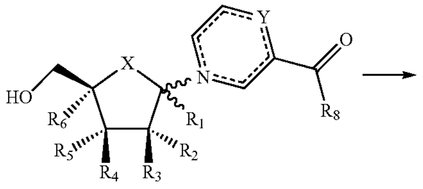

A

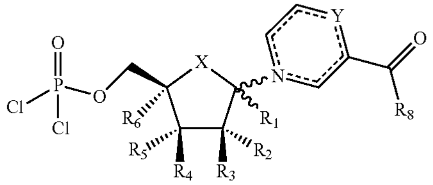

B wherein X, $R_1$, $R_2$, $R_3$, $R_4$, $R_5$, $R_6$, $R_8$, Y, ⚋ and ∿∿ are as described herein above.

In a second step, the phosphorodichloridate of Formula (B) is hydrolyzed to yield the phosphate of Formula (C):

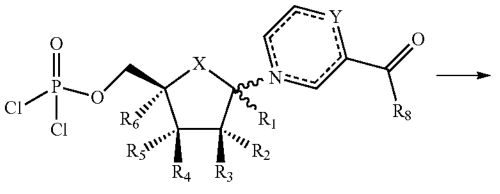

B

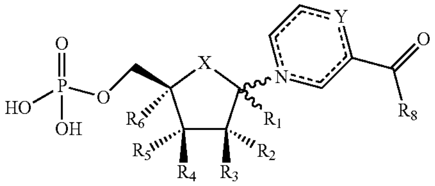

C wherein X, $R_1$, $R_2$, $R_3$, $R_4$, $R_5$, $R_6$, $R_7$, $R_8$, Y, ⚋ and ∿∿ are as described herein above.

In an alternative embodiment, when in Formula (I) $R_7$ is

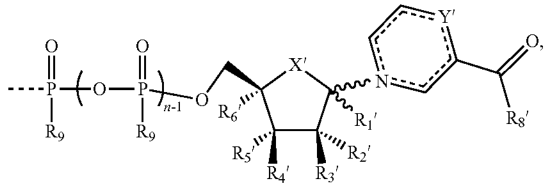

the phosphate compound of Formula (C) obtained in the second step is then reacted, with a phosphorodichloridate compound of Formula (B') obtained as described in the first step:

B'

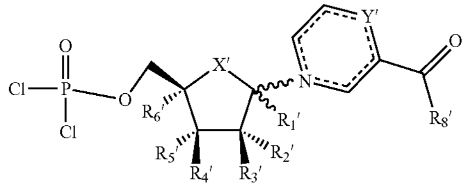

wherein $R_{1'}$, $R_{2'}$, $R_{3'}$, $R_{4'}$, $R_{5'}$, $R_{6'}$, $R_{8'}$, X', Y', ⚋ and ∿∿ are as described herein above; to give the compound of Formula (I) as described herein above, followed by hydrolysis to yield to the compound of Formula (I).

According to one embodiment, the compound of Formula (A) is synthesized using various methods known to the person skilled in the art.

According to one embodiment, the compound of Formula (A) wherein Y is CH, referred to as compound of Formula (A-a), is synthesized by reacting the pentose of Formula (D) with a nitrogen derivative of Formula (E) leading to the compound of Formula (A-1), which is then selectively de protected to give the compound of Formula (A-a),

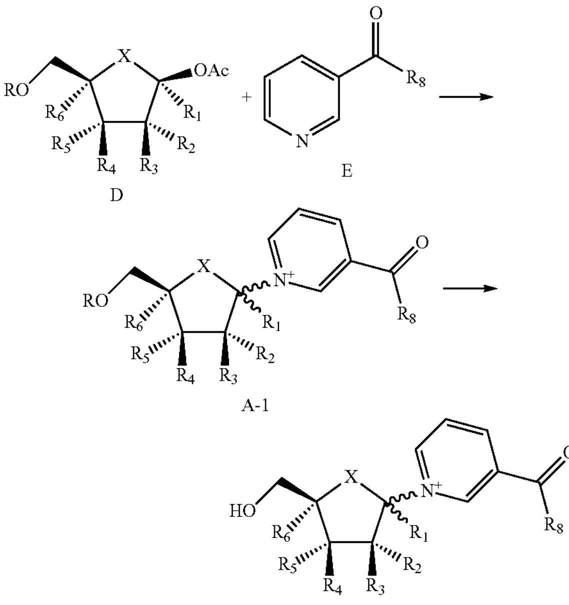

D E A-1 A-a wherein X, $R_1$, $R_2$, $R_3$, $R_4$, $R_5$, $R_6$, $R_8$, Y, ⎓ and ∿∿ are as described herein above and R is a protective group.

According to one embodiment, R is an appropriate protective group known to the skilled person in the art. In one embodiment, the protecting group is selected from triarylmethyls and silyls. Non-limiting examples of triarylmethyl include trityl, monomethoxytrityl, 4,4'-dimethoxytrityl and 4,4',4"-trimethoxytrityl. Non-limiting examples of silyl groups include trimethylsilyl, tert-butyldimethylsilyl, triisopropylsilyl, tert-butyldiphenylsilyl, tri-iso-propylsilyloxymethyl and [2-(trimethylsilyl)ethoxy]methyl.

According to one embodiment, any hydroxyl group attached to the pentose is protected by an appropriate protective group known to the person skilled in the art.

The choice and exchange of protective groups is the responsibility of the person skilled in the art. Protective groups can also be removed by methods well known to the skilled person, for example, with an acid (e.g. mineral or organic acid), base or fluoride source.

According to a preferred embodiment, the nitrogen nicotinamide of Formula (E) is coupled to the pentose of Formula (D) by a reaction in the presence of a Lewis acid leading to the compound of Formula (A-1). Non-limiting examples of Lewis acids include TMSOTf, $BF_3{\cdot}OEt_2$, $TiCl_4$ and $FeCl_3$.

According to one embodiment, the method of the present invention further comprises a step of reducing the compound of Formula (A-a) by various methods well known to the skilled person in the art, leading to the compound of Formula (A-b) wherein Y is $CH_2$ and X, $R_1$, $R_2$, $R_3$, $R_4$, $R_5$, $R_6$, $R_8$, ⎓ and ∿∿ are as defined above.

According to a specific embodiment, the present invention relates to a method for the preparation of the compounds 001, 003, 005, 007 and 009.

In a first step, the nicotinamide of Formula (E-i) is coupled to the ribose tetraacetate of Formula (D-i) by a coupling reaction in the presence of a Lewis acid, resulting in the compound of Formula (A-1-i):

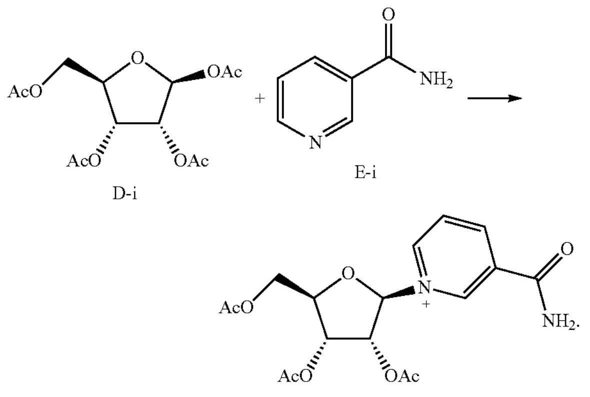

D-i E-i A-1-i

In a second step, an ammoniacal treatment of the compound of Formula (A-1-i) is carried out, leading to the compound 005:

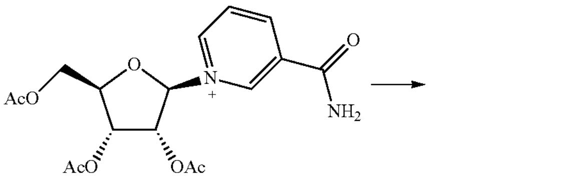

A-1-i 005

In a third step, the mono-phosphorylation of compound 005, in the presence of phosphoryl chloride and a trialkyl phosphate, leads to the phosphorodichloridate of Formula (B-i):

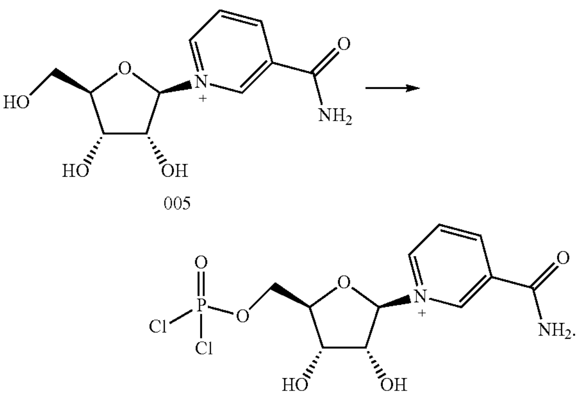

005 B-i

In a fourth step, the phosphorodichloridate of Formula (B-i) is hydrolyzed to yield the compound 001:

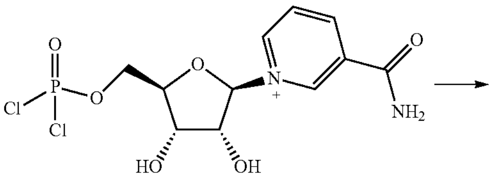

B-i

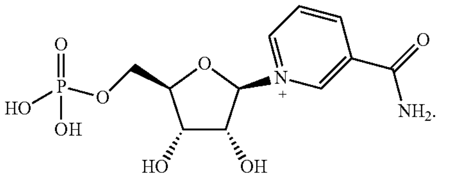

001

Alternatively, in a fifth step, the phosphate compound 001 obtained in the fourth step is then reacted, with the phosphorodichloridate compound of Formula (B-i) obtained as described in the third step, to give compound 009.

According to one embodiment, a step of reducing compound 005 A-2 is carried out, leading to compound 007.

The compound of formula 007 is then monophosphorylated as described in the fourth step and hydrolyzed to the compound 003.

The above method for the preparation of the compounds 001, 003, 005 and 007 can be easily adapted to the synthesis of compounds 002, 004, 006 and 008 by using the suitable starting ribose tetraacetate of Formula (D-ii):

D-ii

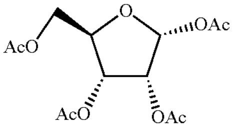

The above method for the preparation of the dimer compound 009 can be easily adapted to the synthesis of dimer compounds 010-014 by using corresponding suitable phosphorodichloridate and phosphate intermediates.

Treatment of Antineoplastic-Induced Toxicity

As mentioned above, there is an unmet need for the treatment of drug-induced toxicities, especially antineoplastic-induced toxicities. This is thus an object of the present invention to provide a treatment of drug-induced toxicities, especially antineoplastic-induced toxicities, for subjects in need thereof. Especially, the present invention relates to the nicotinamide mononucleotide derivatives defined hereinabove for use in the treatment of drug-induced toxicities, especially antineoplastic-induced toxicities, in a subject in need thereof.

Drug-Induced Toxicities

According to one embodiment, the toxicity is caused by at least one drug of the class selected from antineoplastic; antidepressant; antiretroviral; antidiabetic; antihypertensive; antiarrhythmic; CNS stimulant; antimalarial; immunosuppressant, such as cyclosporine; antifungal, such as ketoconazole; cytokines; interferon; anabolic-androgenic steroids; adrenergic stimulants, such as ephedrine; neuromodulator, such as catecholamine; COX inhibitor, such as NAISDs and a mixture thereof.

By “antineoplastic” or “antineoplastic agent” it is referred to a drug used to treat cancer. It may also be referred to as a chemotherapeutic agent.

Non-limiting examples of antineoplastic agents include:

- anthracyclines, such as doxorubicin, bleomycin, dactinomycin, daunorubicin, epirubicin, idarubicin, mitomycin, mitoxantrone, plicamycin and valrubicin;
- alkylating agents, such as Altretamine, Bendamustine, Busulfan, Carmustine, Chlorambucil, Cyclophosphamide, Dacarbazine, Ifosfamide, Lomustine, Mechlorethamine, Melphalan, Procarbazine, Streptozocin, Temozolomide, Thiotepa, Trabectedin, Platinum Coordination Complexes, Carboplatin, Cisplatin and Oxaliplatin;
- taxanes, such as cabazitaxel, docetaxel and paclitaxel;
- topoisomerase inhibitors, such as Etoposide, Irinotecan, Teniposide, Topotecan;
- antimetabolites, such as Antifolates: Methotrexate, Pemetrexed, Pralatrexate and Trimetrexate; Purine Analogues: Azathioprine, Cladribine, Fludarabine, Mercaptopurine and Thioguanine; and Pyrimidine Analogues: Azacitidine, Capecitabine, Cytarabine, Decitabine, Floxuridine, 5-Fluorouracil, Gemcitabine and Trifluridine/Tipracil
- protein kinase inhibitors, such as Abemaciclib, Acalabrutinib, Afatinib, Alectinib, Axitinib, Binimetinib, Bortezomib, Bosutinib, Brigatinib, Cabozantinib, Carfilzomib, Ceritinib, Cobimetinib, Copanlisib, Crizotinib, Dabrafenib, Dacomitinib, Dasatinib, Duvelisib, Enasidenib, Encorafenib, Erlotinib, Gefitinib, Gilteritinib, Glasdegib, Ibrutinib, Idelalisib, Imatinib, Ivosidenib, Ixazomib, Lapatinib, Larotrectinib, Lenvatinib, Lorlatinib, Midostaurin, Neratinib, Nilotinib, Niraparib, Olaparib, Osimertinib, Palbociclib, Pazopanib, Ponatinib, Regorafenib, Ribocicib, Rucaparib, Ruxolitinib, Sonidegib, Sorafenib, Sunitinib, Talazoparib, Trametinib, Vandetanib, Vemurafenib and Vismodegib;
- Biologic Response Modifiers, such as Aldesleukin (IL-2), Denileukin Diftitox and Interferon Gamma;
- Histone Deacetylase Inhibitors, such as Belinostat, Panobinostat, Romidepsin and Vorinostat;
- Hormonal Agents, such as Antiandrogens: Abiraterone, Apalutamide, Bicalutamide, Cyproterone, Enzalutamide, Flutamide and Nilutamide; Antiestrogens (including Aromatase Inhibitors): Anastrozole, Exemestane, Fulvestrant, Letrozole, Raloxifene, Tamoxifen and Toremifene; Gonadotropin Releasing Hormone Analogues: Degarelix, Goserelin, Histrelin, Leuprolide and Triptorelin; and Peptide Hormones: Lanreotide, Octreotide and Pasireotide;
- monoclonal antibodies, such as Alemtuzumab, Atezolizumab, Avelumab, Bevacizumab, Blinatumomab, Brentuximab, Cemiplimab, Cetuximab, Daratumumab, Dinutuximab, Durvalumab, Elotuzumab, Gemtuzumab, Inotuzumab Ozogamicin, Ipilimumab, Mogamulizumab, Moxetumomab Pasudotox, Necitumumab, Nivolumab, Ofatumumab, Olaratumab, Panitumumab, Pembrolizumab, Pertuzumab, Ramucirumab, Rituximab, Tositumomab, and Trastuzumab;
- Vinca Alkaloids, such as Vinblastine, Vincristine, Vinorelbine; and
- other anticancer agents, such as Mitomycin, Bortezomib, Estramustine, Ixabepilone, Asparaginase (Pegaspargase), Bexarotene, Eribulin, Everolimus, Hydroxyurea, Ixabepilone, Lenalidomide, Mitotane, Omacetaxine, Pomalidomide, Tagraxofusp, Telotristat, Temsirolimus, Thalidomide and Venetoclax.

Non-limiting examples of antidepressant agents include:

- Tricyclic antidepressant, such as amitriptyline, clomipramine, amoxapine, desipramine, doxepin, imipramine, nortriptyline, protriptyline and trimipramine
- Tetracyclic antidepressants, such as amoxapine, maprotiline, mianserin, mirtazapine and septiline;
- Selective serotonin reuptake inhibitors, such as citalopram, escitalopram, fluoxetine, fluoxetine, fluvoxamine, paroxetine and sertraline;
- Serotonin-norepinephrine reuptake inhibitors, such as desvenlafaxine, duloxetine, levomilnacipran, milnacipran and venlafaxine;
- Serotonin modulator and stimulators, such as vilazodone and vortioxetine;
- Serotonin antagonist and reuptake inhibitors, such as nefazodone and trazodone;
- Norepinephrine reuptake inhibitors, such as atomoxetine, reboxetine, teniloxazine and viloxazine;
- Norepinephrine-dopamine reuptake inhibitors, such as bupropion; and
- Monoamine oxidase inhibitors, such as isocarboxazid, phenelzine and tranylcypromine.

Non-limiting examples of antiretroviral agents include nucleoside reverse transcriptase inhibitors, such as zidovudine.

Non-limiting examples of antihypertensive agents include:

- calcium channel blockers of the class selected from dihydropyridine, such as nifedipin; phenylethylamine, such as verapamil; and benzothizepine, such as dilitiazem;
- Beta-Adrenoceptor antagonist, such as isoproterenol;

Non-limiting examples of CNS stimulant include methylphenidate, amphetamine and methamphetamine.

According to a preferred embodiment, the drug-induced toxicity is an antineoplastic-induced toxicity.

This invention thus relates to a nicotinamide mononucleotide derivative as described hereinabove for use in the treatment of an antineoplastic-induced toxicity.

According to one embodiment, the toxicity is caused by at least one antineoplastic agent selected from anthracycline drugs, alkylating agents, taxanes, antimetabolites, monoclonal antibodies, tyrosine kinase inhibitors and a mixture thereof. According to one embodiment, the antineoplastic-induced toxicity is caused by at least one drug selected from anthracyclines, alkylating agents, taxanes, antimetabolites, Biologic Response Modifiers, Histone Deacetylase Inhibitors, Hormonal Agents, vinca alkaloids, topoisomerase inhibitors, monoclonal antibodies and tyrosine kinase inhibitors and a mixture thereof.

According to a preferred embodiment, the antineoplastic-induced toxicity is an anthracycline-induced toxicity caused by at least one agent selected from doxorubicin, daunorubicin, epirubicin, idarubicin, mitoxantrone and valrubicin.

According to a more preferred embodiment, the antineoplastic-induced toxicity is an anthracycline-induced toxicity caused by doxorubicin.

Thus, according to one embodiment, the nicotinamide mononucleotide derivative as described above is for use in the treatment of an antineoplastic-induced toxicity. According to a preferred embodiment, the nicotinamide mononucleotide derivative as described above is for use in the treatment of an anthracycline-induced toxicity. According to a more preferred embodiment, the nicotinamide mononucleotide derivative as described above is for use in the treatment of a doxorubicin-induced toxicity.

According to one embodiment, the toxicity as described hereinabove is an acute toxicity. According to one embodiment, the toxicity as described hereinabove is a chronic toxicity.

According to one embodiment, the toxicity as described hereinabove is selected from cardiotoxicity, nephrotoxicity, neurotoxicity, haematotoxicity, hepatotoxicity, lymphoid toxicity, gastrointestinal toxicity, dermal toxicity, metabolic toxicity, ototoxicity, reproductive toxicity, bone toxicity, genetic toxicity and bladder toxicity. According to one embodiment, the toxicity as described hereinabove is selected from cardiotoxicity, nephrotoxicity, haematotoxicity, hepatotoxicity, lymphoid toxicity, gastrointestinal toxicity, dermal toxicity, metabolic toxicity, reproductive toxicity, bone toxicity, genetic toxicity and bladder toxicity.

In one embodiment, the toxicity is not a neurotoxicity. In one embodiment, the toxicity is not an ototoxicity.

According to a preferred embodiment, the toxicity is a cardiotoxicity.

According to one embodiment, the cardiotoxicity is selected from heart failure, left ventricular failure, myocardial ischemia, myocardial infarction, hypokalemia, QT prolongation, torsade de pointes, arrhythmias, pericarditis, myocarditis, bradycardia, hypertension and thromboembolism.

According to one embodiment, the cardiotoxicity is not arrhythmia.

The present invention also concerns a pharmaceutical composition comprising at least one compound for use of the invention, as described hereinabove, and at least one pharmaceutically acceptable carrier for use in the treatment of a toxicity as described hereinabove.

Subjects in Need of Treatment

Preferably, the subject in need of therapeutic and/or preventive treatment is a warm-blooded animal, more preferably a human. According to one embodiment, the subject is a male. According to one embodiment, the subject is a female.

According to one embodiment, the subject is an adult, i.e. over 18 years of age. According to one embodiment, the subject is a child, i.e. under 18 years of age. According to one embodiment, the subject is an infant, i.e. having an age of more than one month and less than two years. According to one embodiment, the subject is a newborn, i.e. having an age from birth to less than one month.

According to a preferred embodiment, the subject is of greater than 50, 55, 60, 65, 70, 75, 80, 85, 90 or 95 years of age. In one embodiment, the subject is of greater than 65, 70, 75, 80, 85, 90 or 95 years of age.

According to another preferred embodiment, the subject is of less than 20, 15, 10 or 5 years of age. In one embodiment, the subject is of less than 18, 17, 16, 15, 14, 13, 12, 11, 10, 9, 8, 7, 6, 5, 4, 3 or 2 years of ages.

According to one embodiment, the subject is receiving or will receive a drug susceptible to induce a toxicity as described above, for the treatment of a condition for which he is in need thereof. Especially, the subject is receiving or will receive an antineoplastic agent as described above.

According to one embodiment, the subject is receiving or will receive a treatment of at least one drug susceptible to induce a toxicity as described above at a cumulative dose, preferably an annual cumulative dose, of greater than 100 $mg/m^2$, 200 $mg/m^2$, 300 $mg/m^2$, 400 $mg/m^2$, 500 $mg/m^2$, 600 $mg/m^2$, 700 $mg/m^2$, 800 $mg/m^2$, 900 $mg/m^2$ or 1000 $mg/m^2$.

In one embodiment, the subject in need receives a treatment of at least one drug as described above at a cumulative dose of greater than 400 $mg/m^2$, 500 $mg/m^2$, 600 $mg/m^2$, 700 $mg/m^2$, 800 $mg/m^2$, 900 $mg/m^2$ or 1000 $mg/m^2$.

According to one embodiment, the subject does not suffer from any underlying pathology.

According to one embodiment, the subject is at risk of developing a toxicity as described above. According to one embodiment, the subject is at risk of developing a toxicity caused by at least one drug as described above. According to one embodiment, the subject is at risk of developing a toxicity caused by at least one antineoplastic agent. According to one embodiment, the subject is at risk of developing a toxicity caused by at least one anthracycline agent. According to one embodiment, the subject is at risk of developing a toxicity caused by doxorubicin.

According to one embodiment, the subject is at risk of developing a cardiotoxicity. According to one embodiment, the subject is at risk of developing a cardiotoxicity caused by at least one drug as described above. According to one embodiment, the subject is at risk of developing a cardiotoxicity caused by at least one antineoplastic agent. According to one embodiment, the subject is at risk of developing a cardiotoxicity caused by at least one anthracycline agent. According to one embodiment, the subject is at risk of developing a cardiotoxicity caused by doxorubicin.

According to one embodiment, the subject is suffering from at least one risk factor i.e. a preexisting disease, condition, habit or behavior that may lead to an increased risk of developing a toxicity, especially a drug-induced toxicity.

According to one embodiment, the subject presents at least one risk factor selected from active chemotherapy, concomitant radiotherapy or cardiac irradiation, concomitant treatment, previous procedures, such as coronary artery bypass graft, angioplasty, vascular stent, previous left ventricular dysfunction, myocardial infarction, angina pectoris, congestive heart failure or cardiovascular comorbidity, genetic predisposition, autoimmune diseases or conditions, cardiovascular diseases or conditions, active smoking, chronic passive smoking (also referred to as environmental exposure smoking), alcohol abuse, drug addiction, obesity (BMI>35), cystic fibrosis, diabetes, dyslipidemia, high blood pressure, renal insufficiency, immunodeficiency, immunosuppression, immunotherapy or antibody treatment for cancer, active infection with Hepatitis B virus (HBV), Hepatitis C virus (HCV) or Human Immunodeficiency Virus (HIV), pregnant women in particular pregnant women who have significant heart disease (whether congenital or acquired), pulmonary hypertension, physical inactivity, patient below 4 years of age, patient above 65 years of age.

According to one embodiment, the subject has developed a toxicity as described above. According to one embodiment, the subject has developed a toxicity induced by at least one drug as described above. According to one embodiment, the subject has developed a toxicity caused by at least one antineoplastic agent. According to one embodiment, the subject has developed a toxicity caused by at least one anthracycline agent. According to one embodiment, the subject has developed a toxicity caused by doxorubicin.

According to one embodiment, the subject is suffering from at least one comorbidity, i.e. a disease or condition coexisting with a toxicity.

According to one embodiment, the subject presents at least one comorbidity selected from hypertension, coronary artery disease, atrial fibrillation, diabetes, chronic kidney failure, cerebrovascular disease, anemia and obesity.

According to one embodiment, the subject in need of therapeutic and/or preventive treatment according to the invention is diagnosed by a health professional. For example, cardiotoxicity is diagnosed by any examination routinely carried out in the medical setting, including echocardiogram, and aim to identify the global or regional decrease of systolic function i.e. a fall in left ventricular ejection fraction by >10% points to a value of less than <50% is commonly used as the decision threshold to define cardiotoxicity.

Alternatively, the cardiotoxicity severity may be assessed based on the measurement of the mean resting corrected QT interval obtained from three consecutive ECGs, as follow:

QTc less than 330 ms=very short QT;

QTc between 330 ms and 370 m=short QT;

QTc between 370 ms and 400 ms=normal QT;

QTc between 400 ms and 460 ms=long QT possible;

QTc between 460 ms and 470 ms=long QT; and

QTc more than 470 ms=very long QT.

According to one embodiment, the subject presents a QTc less than 330 ms. In one embodiment, the subject presents a QTc between 330 ms and 370 m. In one embodiment, the subject presents a QTc between 400 ms and 460 ms. In one embodiment, the subject presents a QTc between 460 ms and 470 ms. In one embodiment, the subject presents QTc more than 470 ms.

According to their clinical manifestation, cardiotoxic events may be classified into three types:

(1) acute cardiotoxicity, i.e. occurring during or immediately after treatment and characterized by depression of myocardial contractility that may be reversible within one week when discontinuing the chemotherapeutic treatment;

(2) early-onset chronic progressive cardiotoxicity, i.e. characterized by systolic or diastolic ventricular dysfunction within one year after the completion of chemotherapeutic treatment; and (3) late-onset chronic progressive cardiotoxicity, i.e. characterized by cardiac dysfunction after a latency period of one or more years following the completion of chemotherapeutic treatment.

According to one embodiment, the subject suffers from acute cardiotoxicity. According to one embodiment, the subject suffers from early-onset chronic progressive cardiotoxicity. According to one embodiment, the subject suffers from late-onset chronic progressive cardiotoxicity.

Therapeutic Effect

According to one embodiment, the use of a nicotinamide mononucleotide derivative as described above prevents, reduces, alleviates, and/or slows down (lessens) one or more of the symptoms of drug-induced toxicities, especially antineoplastic-induced toxicity, more particularly antineoplastic-induced cardiotoxicity.

According to one embodiment, the compound for use as described above reduces the risk that the subject experience toxicity induced by at least one drug as described above by at least 1% to 10%. In one embodiment, the compound for use as described above reduces the risk of toxicity by at least 11% to 20%. In one embodiment, the compound for use as described above reduces the risk of toxicity by at least 21% to 30%. In one embodiment, the compound for use as described above reduces the risk of toxicity by at least 31% to 40%. In one embodiment, the compound for use as described above reduce the risk of toxicity by at least 41% to 50%. In one embodiment, the compound for use as described above reduces the risk of toxicity by at least 51% to 60%. In one embodiment, the compound for use as described above reduces the risk of toxicity by at least 61% to 70%. In one embodiment, the compound for use as described above reduces the risk of toxicity by at least 71% to 80%. In one embodiment, the compound for use as described above reduces the risk of toxicity by at least 81% to 90%. In one embodiment, the compound for use as described above reduces the risk of toxicity by at least 91% to 100%.

Method of Administration

The compounds of the invention as describes hereinabove, may be administered by oral, parenteral (e.g., intramuscular, intraperitoneal, intravenous, ICV, intracisternal injection or infusion, subcutaneous injection, or implant), by inhalation spray, nasal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals, such as mice, rats, horses, cattle, sheep, dogs, cats, monkeys, etc., the compounds of the invention are effective for use in humans. The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term “composition” is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material, such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin. Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant, such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavouring and colouring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer’s solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids, such as oleic acid find use in the preparation of injectables. The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the present invention are employed. (For purposes of this application, topical application shall include mouthwashes and gargles.)

Dosing Regimen

In the treatment of toxicity, preferably cardiotoxicity, an appropriate dosage level for the nicotinamide mononucleotides derivatives of the invention will generally be about 0.01 to 500 mg per kg patient body weight per day which can be administered in single or multiple doses. Preferably, the dosage level will be about 0.1 to about 350 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated.

According to one embodiment, the subject in need thereof receives a treatment of at least one nicotinamide mononucleotide derivative as described above at a cumulative dose, preferably an annual cumulative dose, of greater than 100 mg/kg, 200 mg/kg, 300 mg/kg, 400 mg/kg, 500 mg/kg, 600 mg/kg, 700 mg/kg, 800 mg/kg, 900 mg/kg, 1000 mg/kg, 2500 mg/kg or 5000 mg/kg. In one embodiment, the subject in need thereof receives a treatment of at least one nicotinamide mononucleotide derivative as described above at a cumulative dose, preferably an annual cumulative dose, of greater than 400 mg/kg, 500 mg/kg, 600 mg/kg, 700 mg/kg, 800 mg/kg, 900 mg/kg, 1000 mg/kg, 2500 mg/kg or 5000 mg/kg.

The nicotinamide mononucleotide derivative may be administered on a regimen of 1 to 4 times per day, preferably once, twice or three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Monotherapy/Combination Therapy

The nicotinamide mononucleotide derivatives of the invention may be used in monotherapy or in combination therapy in a subject in need of therapeutic and/or preventive treatment. Thus, according to a first embodiment, the nicotinamide mononucleotide derivative for use of the invention is administered to the subject without any other active ingredient. According to a second embodiment, the nicotinamide mononucleotide derivative for use of the invention is administered to the subject in combination with at least one other active ingredient.

In one embodiment, the compound is administrated to the subject sequentially, simultaneously and/or separately with the other active ingredient.

In one embodiment, the other active ingredient is selected from natural extracts; antineoplastic agents; antidepressant; antiretroviral; beta blockers; antidiabetic; diuretics; antihypertensive; antiarrhythmic; CNS stimulant; antimalarial; immunosuppressant; antifungal; cytokines; interferon; anabolic-androgenic steroids; adrenergic stimulants; neuromodulator, COX inhibitor, angiotensin-converting enzyme inhibitors; angiotensin receptor blockers; ranolazine; metformin; mineralocorticoid receptor antagonists; hydroxymethylglutaryl-coenzyme A reductase inhibitors; antioxidants such as self-nanoemulsifying formulation of quercetin; Q10 coenzyme; vitamin E; L-carnitine; steroids; cyclosporine; mycophenolate mofetil; Anti-TNF such as Infliximab or Etanercept; Anti-Il1 such as Sraninka; Anti-PGF such as Gleevec; Anti-CD20 such as Rituximab; Maltol; PTEN modulators; Nobiletin; pyrroloquinoline quinone; urolithins In one embodiment, the other active ingredient is selected from antineoplastic agents; antidepressant; antiretroviral; beta blockers; antidiabetic; diuretics; antihypertensive; antiarrhythmic; CNS stimulant; antimalarial; immunosuppressant; antifungal; cytokines; interferon; anabolic-androgenic steroids; adrenergic stimulants; neuromodulator; COX inhibitor; angiotensin-converting enzyme inhibitors; angiotensin receptor blockers; ranolazine; metformin; mineralocorticoid receptor antagonists; hydroxymethylglutaryl-coenzyme A reductase inhibitors; antioxidants such as self-nanoemulsifying formulation of quercetin; Q10 coenzyme; vitamin E; L-carnitine; steroids; cyclosporine; mycophenolate mofetil; Anti-TNF such as Infliximab or Etanercept; Anti-Il1 such as Sraninka; Anti-PGF such as Gleevec; Anti-CD20 such as Rituximab; Maltol; PTEN modulators; Nobiletin; pyrroloquinoline quinone; urolithins.

In one embodiment, the other active ingredient is a natural extract, such as for example glycoproteins extract; terpenoids extract containing pentacyclic triterpenes such as betulin, pentacyclic triterpene metabolite such as betulinic acid, transpiroins, rosenolactones, sesquiterpenes, erinacins; a flavonoid extract containing flavones, flavonols, flavanones, flavanols bioflavonoids or isoflavonoids; a polysaccharide extract containing PSP, PSK, CVG, HPB-3, H6PC20; or a polyaromatic molecule such as Hericerins and hericenones; from species such as *Trametes versicolor, Hericium erinaceus, Grifola frondosa*, milk thistle, artichoke, turmeric, dandelion, yellow dock, beetroot and ginger.

According to one embodiment, the pharmaceutical composition of the invention further comprises at least another active ingredient. According to one embodiment, the pharmaceutical composition for use of the invention comprises, in addition to the at least one compound for use of the invention, at least one additional active ingredient, e.g., an active ingredient selected from a natural extract; antineoplastic agents; antidepressant; antiretroviral; beta blockers; antidiabetic; diuretics; antihypertensive; antiarrhythmic; CNS stimulant; antimalarial; immunosuppressant; antifungal; cytokines; interferon; anabolic-androgenic steroids; adrenergic stimulants; neuromodulator; COX inhibitor; angiotensin-converting enzyme inhibitors; angiotensin receptor blockers; ranolazine; metformin; mineralocorticoid receptor antagonists; hydroxymethylglutaryl-coenzyme A reductase inhibitors; antioxidants such as self-nanoemulsifying formulation of quercetin; Q10 coenzyme; vitamin E; L-carnitine; steroids; cyclosporine; mycophenolate mofetil; Anti-TNF such as Infliximab or Etanercept; Anti-Il1 such as Sraninka; Anti-PGF such as Gleevec; Anti-CD20 such as Rituximab; Maltol; PTEN modulators; Nobiletin; pyrroloquinoline quinone; urolithins.

According to one embodiment, the pharmaceutical composition further comprises at least another active ingredient selected from a natural extract. Non limiting example of a natural extract are glycoproteins extract; terpenoids extract containing pentacyclic triterpenes such as betulin, pentacyclic triterpene metabolite such as betulinic acid, transpiroins, rosenolactones, sesquiterpenes, erinacins; a flavonoid extract containing flavones, flavonols, flavanones, flavanols bioflavonoids or isoflavonoids; a polysaccharide extract containing PSP, PSK, CVG, HPB-3, H6PC20; or a polyaromatic molecule such as Hericerins and hericenones; from species such as *Trametes versicolor, Hericium erinaceus, Grifola frondosa*, milk thistle, artichoke, turmeric, dandelion, yellow dock, beetroot and ginger.

Kit of Part

Another object of the invention is a kit-of-parts comprising a first part comprising a nicotinamide mononucleotide derivative of the invention as described hereinabove, and a second part comprising another active ingredient, e.g., an active ingredient selected from a natural extract; antineoplastic agents; antidepressant; antiretroviral; beta blockers; antidiabetic; diuretics; antihypertensive; antiarrhythmic; CNS stimulant; antimalarial; immunosuppressant; antifungal; cytokines; interferon; anabolic-androgenic steroids; adrenergic stimulants; neuromodulator, COX inhibitor; angiotensin-converting enzyme inhibitors; angiotensin receptor blockers; ranolazine; metformin; mineralocorticoid receptor antagonists; hydroxymethylglutaryl-coenzyme A reductase inhibitors; antioxidants such as self-nanoemulsifying formulation of quercetin; Q10 coenzyme; vitamin E; L-carnitine; steroids; cyclosporine; mycophenolate mofetil; Anti-TNF such as Infliximab or Etanercept; Anti-Il1 such as Sraninka; Anti-PGF such as Gleevec; Anti-CD20 such as Rituximab; Maltol; PTEN modulators; Nobiletin; pyrroloquinoline quinone; urolithins.

In one embodiment, the kit-of-parts of the invention comprises a first part comprising compound 001, or a pharmaceutically acceptable salt or solvate thereof, and a second part comprising another active ingredient, e.g., an active ingredient as described hereinabove.

Method of Treatment

This invention also relates to the use of a nicotinamide mononucleotide derivative as described hereinabove or a pharmaceutical composition thereof in the treatment of an antineoplastic-induced toxicity as described hereinabove.

This invention also relates to the use of a nicotinamide mononucleotide derivative as described hereinabove in the manufacture of a medicament for the treatment of an antineoplastic-induced toxicity as described hereinabove.

This invention also relates to a method for the treatment of an antineoplastic-induced toxicity as described hereinabove in a subject in need thereof, comprising a step of administrating to said subject a therapeutically effective amount of a nicotinamide mononucleotide derivative as described hereinabove or a pharmaceutical composition thereof.

EXAMPLES

The present invention is further illustrated by the following examples.

Example 1: Synthesis of Compounds of the Invention

Materials and Methods

All materials were obtained from commercial suppliers and used without further purification. Thin-layer chromatography was performed on TLC plastic sheets of silica gel 60F254 (layer thickness 0.2 mm) from Merck. Column chromatography purification was carried out on silica gel 60 (70-230 mesh ASTM, Merck). Melting points were determined either on a digital melting point apparatus (Electrothermal IA 8103) and are uncorrected or on a Kofler bench type WME (Wagner & Munz). IR, $^{1}H$, $^{19}F$ and $^{13}C$ NMR spectra confirmed the structures of all compounds. IR spectra were recorded on a Perkin Elmer Spectrum 100 FT-IR spectrometer and NMR spectra were recorded, using $CDCl_3$, $CD_3CN$, $D_2O$ or DMSO-$d_6$ as solvent, on a Bruker AC 300, Advance DRX 400 and Advance DRX 500 spectrometers, for $^{1}H$, 75 or 100 MHz for $^{13}C$ and 282 or 377 MHz for $^{19}F$ spectra. Chemical shifts (δ) were expressed in parts per million relative to the signal indirectly (i) to $CHCl_3$ (δ 7.27) for $^{1}H$ and (ii) to $CDCl_3$ (δ 77.2) for $^{13}C$ and directly (iii) to $CFCl_3$ (internal standard) (δ 0) for $^{19}F$. Chemical shifts are given in ppm and peak multiplicities are designated as follows: s, singlet; br s, broad singlet; d, doublet; dd, doublet of doublet; t, triplet; q, quadruplet; quint, quintuplet; m, multiplet. The high-resolution mass spectra (HRMS) were obtained from the "Service central d'analyse de Solaize" (Centre national de la recherche scientifique) and were recorded on a Waters spectrometer using electrospray-TOF ionization (ESI-TOF).

GENERAL EXPERIMENTAL PROCEDURES

Step 1: Synthesis of the Compound of Formula (A-1-i)

The compound of Formula (D-i) (1.0 equiv.) is dissolved in dichloromethane. Nicotinamide of Formula (E-i)(1.50 equiv.) and TMSOTf (1.55 equiv.) are added at room temperature. The reaction mixture is heated under reflux and stirred until the reaction is complete. The mixture is cooled to room temperature and filtered. The filtrate is concentrated to dryness to give tetraacetate (A-1-i).

Step 2: Synthesis of the Compound 005

Tetraacetate (A-1-i) is dissolved in methanol and cooled to −10° C. Ammonia 4.6 M in methanol (3.0 equivalents) at −10° C. is added and the mixture is stirred at this temperature until the reaction is complete. Dowex HCR (H+) resin is added up to pH 6-7. The reaction mixture is heated to 0° C. and filtered. The resin is washed with a mixture of methanol and acetonitrile. The filtrate is concentrated to dryness. The residue is dissolved in the acetonitrile and concentrated to dryness. The residue is dissolved in the acetonitrile to give a solution of the compound 005.

Step 3: Synthesis of the Compound of Formula (B-i)

The solution of the crude compound 005 in acetonitrile is diluted with trimethyl phosphate (10.0 equivalents). The acetonitrile is distilled under vacuum and the mixture is cooled to −10° C. Phosphorus oxychloride (4.0 equivalents) is added at 10° C. and the mixture is stirred at 10° C. until the reaction is complete.

Steps 4 and 5: Synthesis of the Compounds 001 and 009

The mixture obtained in step 3 above is hydrolyzed by the addition of a 50/50 mixture of acetonitrile and water, followed by the addition of methyl tert-butyl ether. The mixture is filtered and the solid is dissolved in water. The aqueous solution is neutralised by the addition of sodium bicarbonate and extracted with dichloromethane. The aqueous layer is concentrated to dryness to give a crude mixture of compound 001 and compound 009.

Compounds 001 and 009 are separated by purification on Dowex 50wx8 with water elution. The fractions comprising compound 001 are concentrated and further purified by a silica gel chromatographic column. The fractions containing compound 009 are concentrated to dryness. The residue is purified by column chromatography on silica gel (gradient isopropanol/water). Pure fractions are combined and concentrated. The residue is freeze-dried to afford compound 009 as a beige solid.

Characterization of compound 009: $^{31}P$ RMN: δ (ppm, reference 85% $H_3PO_4$: 0 ppm in $D_2O$)=−11.72; $^1H$ RMN: δ (ppm, reference TMS: 0 ppm in $D_2O$)=4.20 (ddd, $J_{H-H}$=11.9, 3.5, 2.4 Hz, 2H), 4.35 (ddd, $J_{H-H}$=11.9, 3.9, 2.2 Hz, 2H), 4.43 (dd, $J_{H-H}$=5.0, 2.6 Hz, 2H), 4.53 (t, $J_{H-H}$=5.0 Hz, 2H), 4.59 (m, 2H), 6.16 (d, $J_{H-H}$=5.4 Hz, 2H), 8.26 (dd, $J_{H-H}$=8.1, 6.3 Hz, 2H), 8.93 (d, $J_{H-H}$=8.1 Hz, 2H), 9.25 (d, $J_{H-H}$=6.2 Hz, 2H), 9.41 (s, 2H); $^{13}C$ RMN: δ (ppm, reference TMS: 0 ppm in $D_2O$)=64.84 ($CH_2$), 70.73 (CH), 77.52 (CH), 87.11 (CH), 99.88 (CH), 128.65 (CH), 133.89 (Cq), 139.84 (CH), 142.54 (CH), 146.04 (CH), 165.64 (Cq); MS (ES+): m/z=122.8 [Mnicotinamide+H]+, 650.8 [M+H]+.

Synthesis of Compound 010

Phosphorus oxychloride (3.0 eq.) is added to trimethylphosphate (20.0 eq.) at −5° C. β-NR chloride (1.0 eq.) is added by portions at −5° C. and the reaction mixture stirred overnight at −5° C. Morpholine (3.0 eq.) is added dropwise at −10/0° C. and the mixture stirred for 2-3 h. α-NMN (compound 002) (1.0 eq.) is then added by portions at −5° C. and the reaction mixture stirred at −5° C. overnight. Hydrolysis is performed by dropwise addition of water (5 vol.) at −10/0° C. and the mixture is stirred until complete homogenization at 10-15° C. The reaction mixture is then extracted with dichloromethane (6*10 vol.) and the aqueous phase neutralized by eluting through Purolite A600E formate form resin (theoretical amount to neutralize HCl coming from $POCl_3$). The eluate is then concentrated on vacuum at 45/50° C. to give the crude containing the α,β-diNMN (compound 010). Elution with water through Dowex 50wx8 100-200 mesh $H^+$ form resin allows removing of some impurities. Fractions containing compound 010 are combined and concentrated on vacuum at 45-50° C. The crude is then purified by preparative chromatography on Luna Polar RP 10 μm stationary phase with elution with a 10 mM $NaH_2PO_4$ aqueous solution. Pure fractions are combined and eluted with water on Purolite C100EH $H^+$ form resin (needed quantity to fully exchange $Na^+$ by $H^+$), then eluted on Purolite A600E acetate form resin (needed quantity to fully exchange $H_2PO_4^-$ by acetate). The eluate is concentrated on vacuum and the residue freeze-dried to afford compound 010 as a white solid.

$^{31}P$ RMN: δ (ppm, reference 85% $H_3PO_4$: 0 ppm in $D_2O$)=−11.87, −11.69, −11.46, −11.29; $^1H$ RMN: δ (ppm, reference TMS: 0 ppm in $D_2O$)=4.10 (ddd, J=11.1, 6.1, 3.1 Hz, 1H), 4.15-4.25 (m, 2H), 4.36 (ddd, J=12.2, 4.4, 2.4 Hz, 1H), 4.40 (dd, J=4.9, 2.4 Hz, 1H), 4.44 (dd, J=5.0, 2.7 Hz, 1H), 4.53 (t, J=5.0 Hz, 1H), 4.5 (m, 1H), 4.85 (m, 1H), 4.92 (t, J=5.3 Hz, 1H), 6.15 (d, J=5.5 Hz, 1H), 6.51 (d, J=5.7 Hz, 1H), 8.14 (dd, J=8.0, 6.3 Hz, 1H), 8.26 (dd, J=8.1, 6.3 Hz, 1H), 8.88 (d, J=8.1 Hz, 1H), 8.92 (d, J=8.1 Hz, 1H), 9.02 (d, J=6.3 Hz, 1H), 9.24 (s, 1H), 9.26 (d, J=6.4 Hz, 1H), 9.40 (s, 1H); $^{13}C$ RMN: δ (ppm, reference TMS: 0 ppm in $D_2O$)=64.83, 64.87 ($CH_2$), 65.30, 65.35 ($CH_2$), 70.65 (CH), 70.74 (CH), 71.92 (CH), 77.51 (CH), 87.03, 87.10 (CH), 87.19, 87.26 (CH), 96.57 (CH), 99.83 (CH), 126.89 (CH), 128.54 (CH), 132.44 (Cq), 133.81 (Cq), 139.85 (CH), 140.92 (CH), 142.50 (CH), 143.49 (CH), 145.06 (CH), 145.97 (CH), 165.64 (Cq), 165.88 (Cq); MS (ES+): m/z=122.8 [Mnicotinamide+H]+, 650.9 [M+H]+.

Synthesis of Compound of Formula 011

Phosphorus oxychloride (3.0 eq.) is added to trimethylphosphate (20.0 eq.) at −5° C. α-NR chloride (1.0 eq.) is added by portions at −5° C. and the reaction mixture stirred overnight at −5° C. Morpholine (3.0 eq.) is added dropwise at −10/0° C. and the mixture stirred for 2-3 h. α-NMN (compound 002) (1.0 eq.) is then added by portions at −5° C. and the reaction mixture stirred at −5° C. overnight. Hydrolysis is performed by dropwise addition of water (5 vol.) at −10/0° C. and the mixture is stirred until complete homogenization at 10-15° C. The reaction mixture is then extracted with dichloromethane (6*10 vol.) and the aqueous phase neutralized by eluting through Purolite A600E formate form resin (theoretical amount to neutralize HCl coming from $POCl_3$). The eluate is then concentrated on vacuum at 45/50° C. to give the crude containing the α,α-diNMN (compound 011). Elution with water through Dowex 50wx8 100-200 mesh $H^+$ form resin allows removing of some impurities. Fractions containing the compound 011 are combined and concentrated on vacuum at 45-50° C. The crude is then purified by preparative chromatography on Luna Polar RP 10 μm stationary phase with elution with a 10 mM $NaH_2PO_4$ aqueous solution. Pure fractions are combined and eluted with water on Purolite C100EH $H^+$ form resin (needed quantity to fully exchange $Na^+$ by $H^+$), then eluted on Purolite A600E acetate form resin (needed quantity to fully exchange $H_2PO_4$ by acetate). The eluate is concentrated on vacuum and the residue freeze-dried to afford compound 011 as a white solid.

$^{31}P$ RMN: δ (ppm, reference 85% $H_3PO_4$: 0 ppm in $D_2O$)=−11.40; $^1H$ RMN: δ (ppm, reference TMS: 0 ppm in $D_2O$)=4.14 (ddd, J=11.4, 3.4, 2.8 Hz, 2H), 4.23 (ddd, J=11.6, 3.3, 2.8 Hz, 2H), 4.44 (dd, J=4.8, 2.3 Hz, 2H), 4.88 (m, 2H), 4.96 (t, J=5.3 Hz, 2H), 6.54 (d, J=5.7 Hz, 2H), 8.15 (dd, J=8.1, 6.2 Hz, 2H), 8.89 (d, J=8.1 Hz, 2H), 9.05 (d, J=6.3 Hz, 2H), 9.26 (s, 2H); $^{13}C$ RMN: δ (ppm, reference TMS: 0 ppm in $D_2O$)=65.37 (CH2), 70.70 (CH), 71.95 (CH), 87.30 (CH), 96.62 (CH), 126.91 (CH), 132.45 (Cq), 140.94 (CH), 143.52 (CH), 145.07 (CH), 165.90 (Cq); MS (ES+): m/z=122.7 [Mnicotinamide+H]+, 650.8 [M+H]+.

Example 2: Evaluation of Compounds of the Invention in a Model of Doxorubicin-Induced Cardiotoxicity The aim of the present study was to evaluate, the effects of i.p. administration of compounds 001, 010 and 011 at 180 mg/kg in the progression of a cardiotoxicity induced by doxorubicin.

I. MATERIALS AND METHODS

Material

Animals: 76 male mice, 8-week-old at the arrival were obtained from Janvier Labs, Le Genest St Isle, 53941 St Berthevin, France. Each animal was identified with electronic chip. Each cage was numbered. Based on the animal number/cage and number of cages, the animals were assigned of unique number with the name of group and mice number. The matching cards that were used to identify cages where experimental animals were housed contained the following information: the name of the experiment, the number of the experiment and the cage number.

Compound: Compounds 001, 010 and 011 were manufactured according to Example 1 or commercially purchased and stored at +4° C. until use. Vehicle was physiological buffer.

Methods

1. Preparation of Formulation:

The powder of compounds 001, 010 and 011 (180 mg/kg) were dissolved in vehicle (the solution is used at room temperature for maximum 1 day). A fresh sample for each administration was prepared every day except the week-end (the solution was prepared on Saturday and used on Saturday and Sunday).

2. Doxorubicin-Induced Cardiotoxicity

Cardiotoxicity was induced by a single intraperitoneal injection of doxorubicin (DOX) at 20 mg/kg. Doxorubicin was prepared at 2 mg/mL and volume of administration was 10 mL/Kg.

Mortality rate was followed-up all along the experimental phase.

3. Experimental Groups

Group Description:

Group 1: Vehicle (i.p.)

Group 2: Doxorubicin (20 mg/kg)

Group 3: Doxorubicin (20 mg/kg)+compound 001 180 mg/kg

Group 4: Doxorubicin (20 mg/kg)+compound 010 180 mg/kg

Group 5: Doxorubicin (20 mg/kg)+compound 011 180 mg/kg

Group Repartition:

Each group involves 14-24 mice.

As set forth in the regulations for Non-clinical Laboratory Studies, test and control animal groups were maintained under identical conditions. The intended duration of study was 11 days.

4. Induction with Doxorubicin

At D0, mice received DOX (20 mg/kg) by intraperitoneal route.

5. Treatment

The treatment with compounds 001, 010 and 011 was initiated from 5 days before DOX injection once per day from D5 to D0.

Mice were i.p treated with compounds 001, 010 and 01130 min before DOX injection.

Mice were i.p treated with compounds 001,010 and 011 for the duration of the experiment (D0 to D5) once per day. Last injection occurred 24 hours before sacrifice.

6. Body Weight, Survival Rate and Clinical Examination

The bodyweight was assessed at inclusion and at D5.

The survival rate was recorded every day until the end of the experiment (D5).

7. Blood and Urine Collection

Retro-orbital blood collection was performed at the inclusion and at 1 and 5 days after the induction with DOX to assess biomarkers (especially LDH).

8. Organs Collection

At D5, heart and tibia were collected.

9. Assessment of Cardiac Function by Echocardiography

Echocardiography (ECG) was performed 5 days after doxorubicin injection in anesthetized (isoflurane 1.5-2%) animals with non-invasive two-dimensional echocardiography (VF16-5 probe, Siemens, Acuson NX3 Elite). After removing hairs on the chest, numeric images of the heart will be obtained in both parasternal long-axis and short axis views.

The following cardiac function were assessed during ECG:

- Left ventricle (LV) end-systolic and end-diastolic inner diameter,
- LV end-systolic and end-diastolic volume,
- Fractional shortening;
- Ejection fraction;
- Heart Rate; and
- Anterior and posterior wall thickness in Diastole and in systole.

II. RESULTS AND DISCUSSION

1. Survival Rate

FIG. 1 shows the percentage of survival of mice induced or not with DOX (20 mg/kg), 5 days after doxorubicin injection.

DOX mice were treated with compounds 001, 010 and 011 (180 mg/kg) or vehicle.

As shown, almost 50% of doxorubicin mice treated with vehicle died before the end of experimental protocol.

Treatment with compound 001 tended to improve the survival rate (78% of survival) without reaching statistical significance probably because of the crossing of survival curves. However, treatment with compounds 010 or 011 significantly improved survival rate (98% and 100% of survival respectively) compared to untreated groups (50% of survival).

2. Body Weight

FIG. 2A shows the body weight evolution of mice treated with compounds 001, 010 and 011 (180 mg/kg) or vehicle, before (light gray symbol) and 5 days after saline solution or DOX (20 mg/kg) injection (dark gray symbol).

FIG. 2B shows the body weight gain calculated as follow: bodyweight at the day of sacrifice minus bodyweight before injection.

Surviving vehicle-treated mice showed major signs of suffering associated with a strong decrease in body weight (−4.2±0.5 g). The body weight loss observed after doxorubicin administration was significantly decreased by compounds 001, 010 and 011 ($p<0.01$, $p<0.001$, $p<0.001$ respectively).

3. Cardiac Function 3.1. Left Ventricle End Diastolic/Systolic Volumes and Election Fraction FIG. 3 shows Left Ventricle (LV) end diastolic (FIG. 3A) and end systolic (FIG. 3B) volumes and ejection fraction (FIG. 3C) 5 days after saline solution or DOX (20 mg/kg) injection, with and without treatment with compounds 001, 010 and 011.

As shown in FIG. 3, doxorubicin induced a significant increase in end-systolic LV (left ventricular) volume (FIG. 3B) without significative difference in end-diastolic (FIG. 3A) when compared to control group leading to a large decrease in ejection fraction (38.9±1.3% in doxorubicin vehicle group vs 64.8±0.6% in control mice) (FIG. 3C).

Compared to DOX-induced animals that received vehicle, compounds 001, 010 and 011 reduced end-systolic LV (FIG. 3B) volume when compared to doxorubicin vehicle group, with statistical significance observed for compound 010 ($p<0.05$).

Compared to untreated DOX animals, ejection fraction was significantly improved after treatment with compounds 001, 010 and 011 (56.9±0.6% in doxorubicin mice treated with NMN ($p<0.05$), 58.2±0.5% in doxorubicin mice treated with compound 011 ($p<0.001$) and 60.0±0.6% in doxorubicin mice treated with compound 010 ($p<0.001$)) (FIG. 3C).

3.2. Left Ventricle End Diastolic/Systolic Diameters, Fractional Shortening and Heart Rate FIG. 4 shows LV end diastolic and end systolic diameters (FIGS. 4A and 4B respectively), fractional shortening (FIG. 4C) and heart rate (FIG. 4D) 5 days after saline solution or DOX (20 mg/kg) injection.

As shown in FIG. 4, in doxorubicin-treated mice, LV internal diameter was significantly increased in systole (FIG. 4B) without significative difference in diastole (FIG. 4A) resulting in a decreased in fractional shortening (33.5±0.4% vs 43.2±0.5% in control mice) (FIG. 4C). Treatment with compounds 001, 010 and 011 significantly improved fractional shortening to around 38% ($p<0.001$ for the three groups).

Moreover, doxorubicin significantly reduced the heart rate when compared to control mice (365.1±23.9 bpm vs 525.6±19.8 bpm respectively). Treatments with compounds 001, 010 and 011 resulted in increased heart rates, with compound 010 significantly improving this parameter (470.1±18.8 bpm ($p<0.001$)).

3.3. Left Ventricle Anterior and Posterior Wall Thickness in Systole and in Diastole FIG. 5 shows LV anterior wall thickness in systole and in diastole (FIGS. 5A and 5B respectively) and posterior wall thickness in systole and in diastole (FIGS. 5C and 5D respectively) 5 days after saline solution or DOX (20 mg/kg) injection.

Doxorubicin significantly decreased anterior and posterior wall thickness in systole but not in diastole, and any of treatments had significant effect.

Treatments with compound 001, 010 and 011 (180 mg/kg) in DOX mice resulted in non-significant increases of anterior and posterior wall thickness in systole.

4. Heart Weight

FIG. 6 shows heart weight (FIG. 6A) and heart weight normalized to tibial length (FIG. 6B) 5 days after saline solution or DOX (20 mg/kg) injection.

DOX mice were treated with compounds 001, 010 and 011 (180 mg/kg) or vehicle.

As shown in FIGS. 6A and 6B, doxorubicin significantly decreased heart weight when compared to control mice (102.3±4.6 mg vs 128.9±3.3 mg respectively). Treatments with compounds 010 and 011 tended to increase heart weight without reaching significance vs DOX vehicle mice. Similar results were obtained when heart weight was normalized to tibia length.

5. Biomarker Assessment

FIG. 7 shows LDH concentrations (U/L, FIG. 7A) and LDH (fold change, FIG. 7B) in the plasma of mice 5 days after saline solution or DOX (20 mg/kg) injection.

DOX mice were treated with compounds 001,010 and 011 (180 mg/kg) or vehicle. Plasmatic LDH (lactate dehydrogenase) was measured 5 days after doxorubicin injection. As shown in FIGS. 7A and 7B, doxorubicin induced cell damage as shown by more than 3-fold increase in LDH release compared to control group. Treatment with NMN decreased LDH release by more than 35% without reaching statistical significance. However, treatment with both compounds 010 and 011 resulted in a significant effect with a reduction in LDH levels by 50-55% ($p<0.05$).

III. CONCLUSION

Altogether, results showed that doxorubicin induced cardiac dysfunction characterized by impaired cardiac contractility and cardiac filling, as well as cell cardiac damage. Doxorubicin also led to high mortality, and a strong body weight loss.

Compounds 001, 010 and 011 treatments significantly improved survival rate, body weight loss and prevented cardiac functions degradation as shown by the effects of treatments on ejection fraction, fractional shortening and heart rate.

The invention claimed is:

1. A method for treating an antineoplastic-induced toxicity in a subject in need thereof, wherein the toxicity is cardiotoxicity, said method comprising administering to said subject a therapeutically effective amount of a compound of Formula (I),

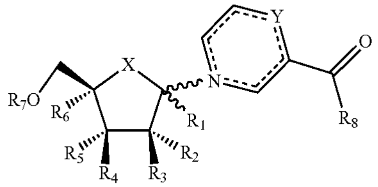

(I)

or a pharmaceutically acceptable salt or solvate thereof; wherein:

X is O;

$R_1$ is H;

$R_2$, $R_3$, $R_4$ and $R_5$ are independently selected from H and hydroxyl;

$R_6$ is H;

$R_7$ is selected from $P(O)R_9R_{10}$, and

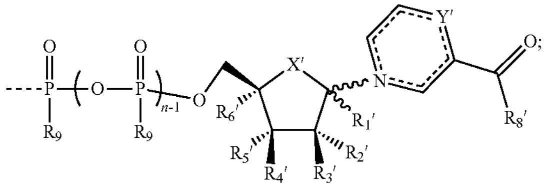

wherein:

$R_9$ and $R_{10}$ are independently selected from OH, and $OR_{11}$; wherein:

$R_{11}$ is selected from $(C_1\text{-}C_{10})$ alkyl, $(C_3\text{-}C_{10})$ cycloalkyl, $(C_5\text{-}C_{12})$ aryl, $(C_1\text{-}C_{10})$ alkyl-$(C_5\text{-}C_{12})$ aryl, substituted $(C_5\text{-}C_{12})$ aryl, $(C_1\text{-}C_{10})$ heteroalkyl, $(C_1\text{-}C_{10})$ haloalkyl, $—(CH_2)_mC(O)$ $(C_1\text{-}C_{15})$ alkyl, $—(CH_2)_mOC(O)$ $(C_1\text{-}C_{15})$ alkyl, $—(CH_2)_mOC(O)O(C_1\text{-}C_{15})$ alkyl, $—(CH_2)_mSC(O)(C_1\text{-}C_{15})$ alkyl, $—(CH_2)_mC(O)O(C_1\text{-}C_{15})$ alkyl, $—(CH_2)_mC(O)O(C_1\text{-}C_{15})$ alkyl-$(C_5\text{-}C_{12})$ aryl; wherein m is an integer selected from 1 to 8; and $—P(O)(OH)OP(O)(OH)_2$; and an internal or external counterion;

X' is O;

$R_{1'}$ is H;

$R_{2'}$, $R_{3'}$, $R_{4'}$ and $R_{5'}$ are independently selected from H, and hydroxyl;

$R_{6'}$ is H;

$R_{8'}$ is $NH_2$;

Y' is selected from CH and $CH_2$;

n is an integer equal to 2;

- - - represents the point of attachment;

$\overline{- - -}$ represents a single or double bond depending on Y'; and

∿∿∿ represents the alpha or beta anomer depending on the position of $R_{1'}$;

$R_8$ is $NH_2$;

Y is selected from CH;

$\overline{- - -}$ represents a single or double bond depending on Y; and

∿∿∿ represents the alpha or beta anomer depending on the position of $R_1$.

2. The method according to claim 1, wherein the compound of formula (I) is selected from:

| Compounds (anomers) | Structure |
|---|---|
| 001 (beta) | 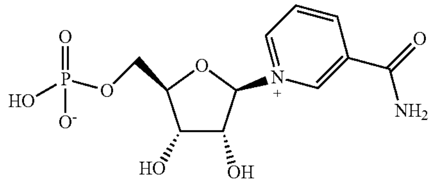 |
| 002 (alpha) | 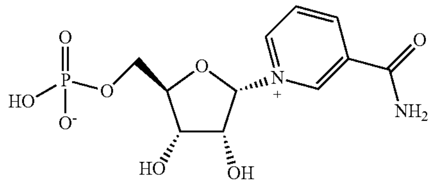 |
| 003 (beta) | 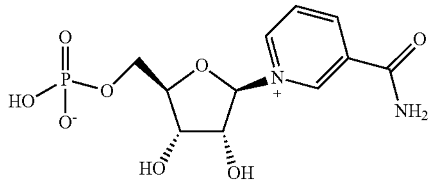 |
| 004 (alpha) | 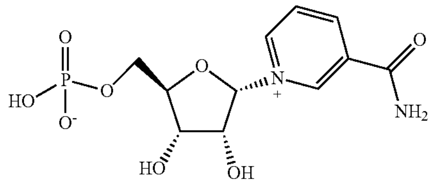 |
| 009 (beta, beta) | 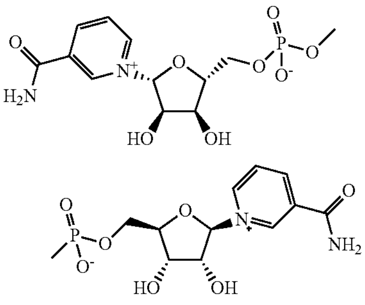 |

-continued

| Compounds (anomers) | Structure |
|---|---|
| 010 (beta, alpha) | 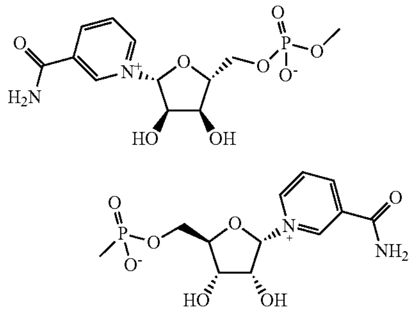 |
| 011 (alpha, alpha) | 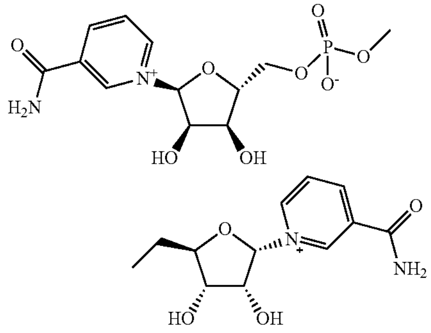 |
| 012 (beta, beta) | 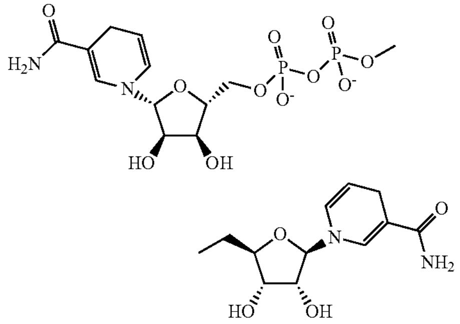 |
| 013 (beta, alpha) | 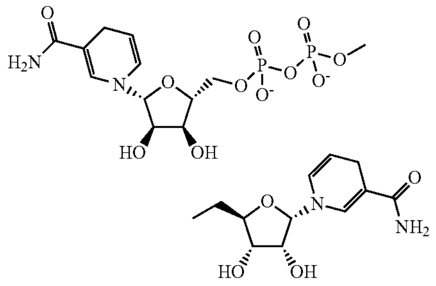 |
| 014 (alpha, alpha) | 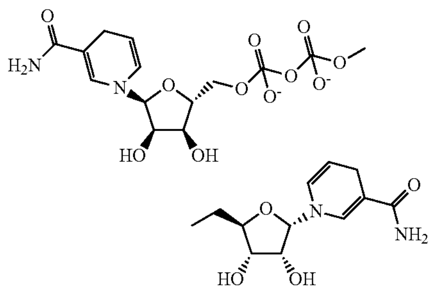 |

and pharmaceutically acceptable salts and solvates thereof.

3. The method according to claim 1, wherein the toxicity is induced by an antineoplastic agent selected from anthracyclines, alkylating agents, taxanes, antimetabolites, Biologic Response Modifiers, Histone Deacetylase Inhibitors, Hormonal Agents, vinca alkaloids, topoisomerase inhibitors, monoclonal antibodies, tyrosine kinase inhibitors and a mixture thereof.

4. The method according to claim 1, wherein the toxicity is induced by an anthracycline selected from doxorubicin, daunorubicin, epirubicin, idarubicin, bleomycin, mitomycin, mitoxantrone, plicamycin and valrubicin.

5. The method according to claim 1, wherein the toxicity is induced by doxorubicin.

6. The method according to claim 1, wherein the cardiotoxicity is selected from the group consisting of heart failure, left ventricular failure, myocardial ischemia, myocardial infarction, QT prolongation, torsade de pointes, arrhythmias, pericarditis, myocarditis, bradycardia, hypertension and thromboembolism.

7. The method according to claim 1, wherein the compound of formula (I) is comprised in a pharmaceutical composition also comprising at least one pharmaceutically acceptable carrier.

8. The method according to claim 7, wherein the pharmaceutical composition further comprises at least one active ingredient selected from the group consisting of a natural extract; antineoplastic agents; antidepressant; antiretroviral; beta blockers; antidiabetic; diuretics; antihypertensive; antiarrhythmic; CNS stimulant; antimalarial; immunosuppressant; antifungal; cytokines; interferon; anabolic-androgenic steroids; adrenergic stimulants; neuromodulator; COX inhibitor; angiotensin-converting enzyme inhibitors; angiotensin receptor blockers; ranolazine; metformin; mineralocorticoid receptor antagonists; hydroxymethylglutaryl-coenzyme A reductase inhibitors; antioxidants; Q10 coenzyme; vitamin E; L-carnitine; steroids; cyclosporine; mycophenolate mofetil; Anti-TNF; Anti-Il1; Anti-PGF; Anti-CD20; Maltol; PTEN modulators; Nobiletin; pyrrolinone quinone; and urolithins.

9. The method according to claim 8, wherein the antioxidant is a self-nanoemulsifying formulation of quercetin; the Anti-TNF is Infliximab or Etanercept; the Anti-Il1 is Sraninka; the Anti-PGF is Gleevec; and the Anti-CD20 is Rituximab.

* * * * *